(12) United States Patent
LeCronier et al.

(10) Patent No.: US 8,771,272 B2
(45) Date of Patent: Jul. 8, 2014

(54) EASILY IMPLANTABLE AND STABLE NAIL-FASTENER FOR SKELETAL FIXATION AND METHOD

(71) Applicants: David LeCronier, Oxford, MI (US); Patrick Atkinson, Grand Blanc, MI (US)

(72) Inventors: David LeCronier, Oxford, MI (US); Patrick Atkinson, Grand Blanc, MI (US)

(73) Assignee: Kettering University, Flint, MI (US)

( * ) Notice: Subject to any disclaimer, the term of this patent is extended or adjusted under 35 U.S.C. 154(b) by 0 days.

(21) Appl. No.: 13/625,595

(22) Filed: Sep. 24, 2012

(65) Prior Publication Data

US 2013/0030436 A1    Jan. 31, 2013

Related U.S. Application Data

(63) Continuation-in-part of application No. 12/818,395, filed on Jun. 18, 2010, now Pat. No. 8,287,540.

(51) Int. Cl.
*A61B 17/56* (2006.01)
*A61B 17/58* (2006.01)
*A61F 2/30* (2006.01)

(52) U.S. Cl.
USPC .............................................. 606/64; 606/62

(58) Field of Classification Search
USPC ............ 606/62–64, 86 R, 87, 90, 95, 99, 105
See application file for complete search history.

(56) References Cited

U.S. PATENT DOCUMENTS

| | | |
|---|---|---|
| 5,454,813 A | 10/1995 | Lawes |
| 5,472,444 A | 12/1995 | Huebner |
| 6,235,031 B1 | 5/2001 | Hodgeman et al. |
| 6,355,043 B1 | 3/2002 | Adam |
| 7,569,055 B2 | 8/2009 | Zander et al. |
| 7,722,611 B2 | 5/2010 | Cavallazzi et al. |
| 2004/0147930 A1 | 7/2004 | Zander et al. |
| 2005/0075637 A1 | 4/2005 | Semet |
| 2006/0084997 A1 | 4/2006 | Dejardin |
| 2006/0173457 A1* | 8/2006 | Tornier ........................... 606/62 |
| 2009/0326533 A1* | 12/2009 | Dell'Oca ........................ 606/64 |

OTHER PUBLICATIONS

Angular Stable Locking System (ASLS); Dated Oct. 2008; 48 Pages; Synthes (www.synthes.com/lit).

(Continued)

*Primary Examiner* — Mary Hoffman
*Assistant Examiner* — Christina Negrellirodrigue
(74) *Attorney, Agent, or Firm* — Dickinson Wright PLLC

(57) ABSTRACT

An intramedullary nail (20) defining a bore (34) is inserted into a medullary canal (26) of a bone (24). A threaded fastener (22) has a compression portion (48) presenting a compression portion diameter ($D_{CP}$) and a threaded portion (50) presenting a threaded portion diameter ($D_{TP}$). The fastener (22) extends through a near cortex hole (40) and/or a far cortex hole (42), and the threaded portion (22) threadedly engages the bore (34). A compression transmission device (54) is disposed between a head (44) of the fastener (22) and the intramedullary nail (20) for transmitting the compressional load of the threaded fastener (22) to the intramedullary nail (20). An interior space of the compression transmission device (54) is greater than the compression portion diameter ($D_{CP}$) providing space about the threaded fastener (22) for allowing the fastener axis (A) to be variously disposed relative to the interior space.

31 Claims, 14 Drawing Sheets

(56) References Cited

OTHER PUBLICATIONS

The Titanium Solid Humeral Nail System Technique Guide; Dated 2001; 70 Pages; Synthes (www.synthes.com/lit).
Comparison of a New Braid Fixation System to an Interlocking Intramedullary Nail for Tribal Osteotomy Repair in an Ovine Model; Yan Lu et al.; Copyright 2009; 10 Pages The American College of Veterinary Surgeons.
Angle Stable Locking Reduces Interfragmentary Movements and Promotes Healing After Unreamed Nailing; K. Kasper et al; Dated Sep. 2005; 11 Pages; The Journal of Bone and Joint Surgery (www.ejbjs.org).

* cited by examiner

FIG. 15A  FIG. 16A

EASILY IMPLANTABLE AND STABLE NAIL-FASTENER FOR SKELETAL FIXATION AND METHOD

CROSS REFERENCE TO RELATED APPLICATION

This application is a continuation-in-part of U.S. patent application Ser. No. 12/818,395, filed Jun. 18, 2010, the entire contents of which is hereby incorporated by reference.

STATEMENT REGARDING FEDERALLY SPONSORED RESEARCH

This invention was made with Government support under contract numbers W81XWH0720119 and W81XWH1120128 awarded by the United States Army Medical Research Acquisition Activity. The Government has certain rights in this invention.

BACKGROUND OF THE INVENTION

1. Field of the Invention

An easily implantable and stable nail-fastener for skeletal fixation to treat bone fractures and to provide support to the long bones and a method for implanting the nail-fastener.

2. Related Art

An intramedullary nail for skeletal fixation of the type to which the subject invention pertains includes a threaded fastener extending through a compression transmission device to threadedly engage the nail. The compression transmission device transmits the compressional load of the threaded fastener to the intramedullary nail during fixation. One such nail-fastener device is illustrated in U.S. Patent Application No. 2009/0326533 to Dell'Oca, which discloses a two-diameter, two-piece locking bolt. The smaller diameter portion or male part of the bolt screws into the larger diameter portion or female part of the bole and threadedly engages the nail. The female part of the two diameter locking bolt abuts the nail to establish compression between the bolt and the nail. The prior art design requires the male part to be coaxial with the female part and near hole of the cortex in the bone. Additionally, there is interdigitation of the male and female parts, thus, they are not independent of one another.

SUMMARY OF THE INVENTION

One aspect of the invention provides a nail-fastener apparatus for implantation into the medullary canal surrounded by the cortex of a bone, wherein the bone includes a near cortex hole. The apparatus includes an intramedullary nail for insertion into the medullary canal. The intramedullary nail extends between a top end and a bottom end and defines a bore. A threaded fastener includes a head and an end with a threaded portion extending along a fastener axis therebetween for extending through the near cortex hole of the bone and threadedly engaging the bore of the intramedullary nail. The threaded fastener also includes a compression portion presenting a compression portion diameter and extending along the fastener axis between the threaded portion and the head for extending through the near cortex hole of the bone. A compression transmission device surrounds the compression portion of the threaded fastener. The compression transmission device has an exterior and an interior defining an interior space. The compression transmission device is disposed between the head of the threaded fastener and the intramedullary nail. The interior space provided by the compression transmission device is greater than the compression portion diameter of the fastener for providing space at least partially about the threaded fastener for allowing the fastener axis to be variously disposed relative to the interior space.

Another aspect of the invention provides the nail-fastener apparatus including the intramedullary nail, the threaded fastener, and the compression transmission device, wherein the threaded fastener extends through the bore of the intramedullary nail and threadedly engages the cortex along a far cortex hole.

Yet another aspect of the invention provides the nail-fastener apparatus with an unthreaded fastener, wherein the unthreaded fastener frictionally engages the bore of the intramedullary nail, the far cortex hole, or both.

Another aspect of the invention provides a method for implanting the intramedullary nail into the medullary canal surrounded by the cortex of the bone. The method includes providing the bore in the intramedullary nail including threads, forming the near cortex hole in the cortex, providing the threaded fastener including the head and the end with the compression portion presenting the compression portion diameter and the threaded portion extending along the fastener axis between the head and the end. The method also includes providing the compression transmission device having the exterior and the interior defining the interior space, disposing the compression transmission device in the near cortex hole and contacting the intramedullary nail with the compression transmission device, extending the threaded fastener through the compression transmission device, and threadedly engaging the threaded portion of the threaded faster to the intramedullary nail along the bore. The method further includes providing the compression transmission device with the interior space being greater than the compression portion diameter of the threaded fastener for providing space at least partially about the threaded fastener for allowing the fastener axis to be variously disposed relative the interior space.

Yet another aspect of the invention provides a method for implanting the intramedullary nail into the medullary canal surrounded by the cortex of the bone, wherein the method comprises forming the far cortex hole in the cortex, extending the threaded fastener through the compression transmission device and the intramedullary nail, and threadedly engaging the threaded portion of the threaded fastener to the cortex along the far cortex hole.

Another aspect of the invention provides a method for implanting the intramedullary nail into the medullary canal surrounded by the cortex of the bone, wherein the compression portion diameter of the threaded fastener is greater than the threaded portion diameter. The method includes forming the near cortex hole in the cortex to present a near cortex hole diameter being greater than the compression portion diameter. The method further includes extending the threaded fastener through the near cortex hole and into the bore of the intramedullary nail until the compression portion of the threaded fastener engages the intramedullary nail, and threadedly engaging the threaded portion of the threaded fastener to the intramedullary nail along the bore.

Yet another aspect of the invention provides a method for implanting the intramedullary nail into the medullary canal surrounded by the cortex of the bone, wherein the unthreaded fastener frictionally engages the bore of the intramedullary nail, the far cortex hole, or both.

BRIEF DESCRIPTION OF THE DRAWINGS

Other advantages of the present invention will be readily appreciated, as the same becomes better understood by reference to the following detailed description when considered in connection with the accompanying drawings wherein:

FIG. 15A is a transverse cross-sectional view of the fastener extending and into the intramedullary nail of FIG. 15;

FIG. 16A is a transverse cross-sectional view of the fastener extending and into the intramedullary nail of FIG. 16 with the counterbore surface;

DETAILED DESCRIPTION OF THE INVENTION

Referring to the Figures, wherein like numerals indicate corresponding parts throughout the several views, an intramedullary nail 20 and fastener 22 for skeletal fixation constructed in accordance with the subject invention is shown in FIGS. 1-26.

Figure 5:
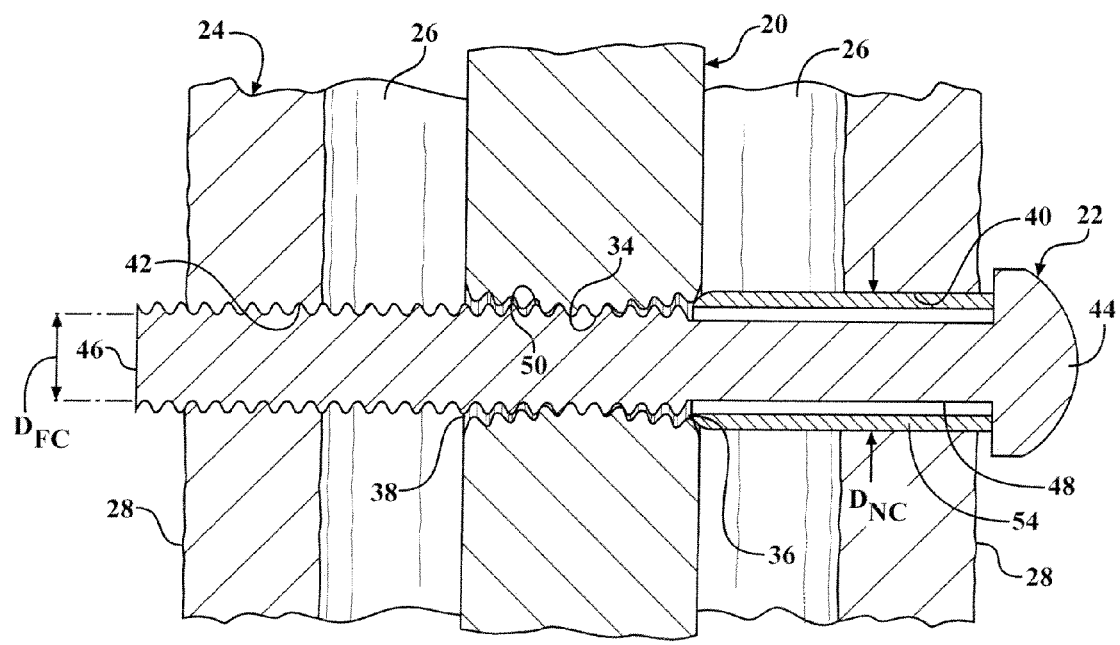
FIG. 5 is an enlarged cross-sectional view of the fastener extending through the compression transmission device and the intramedullary nail and through the far cortex hole and threadedly engaging the bore.
Figure 6:
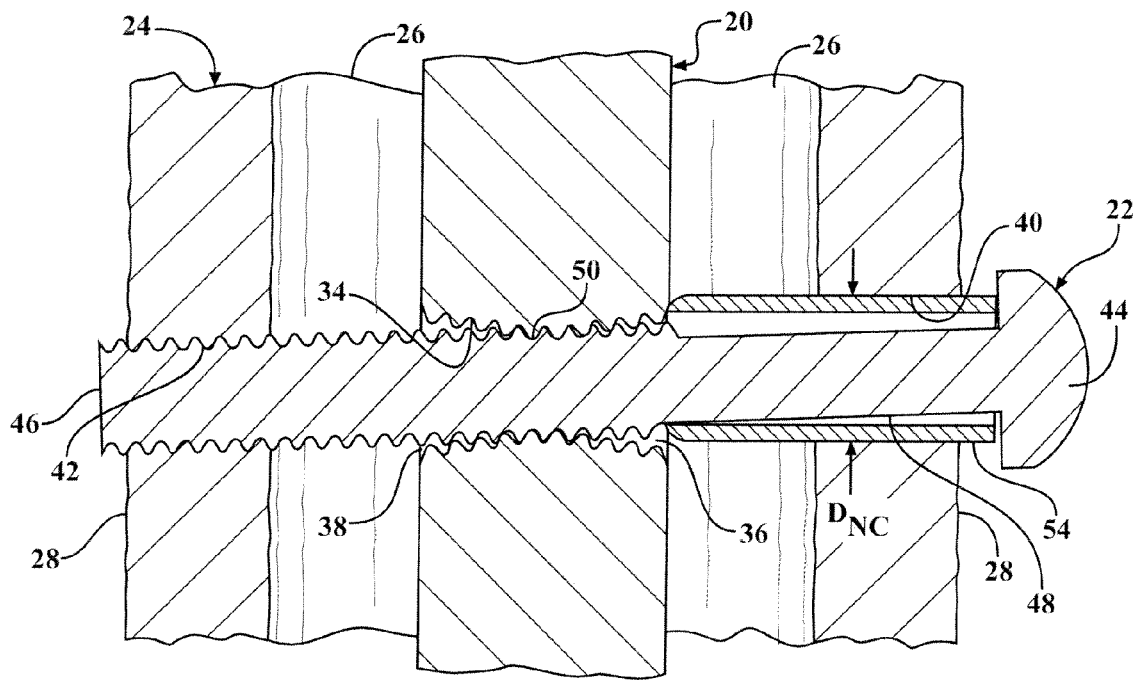
FIG. 6 is a cross-sectional view like FIG. 5 but with the fastener skewed relative to the bore axis and eccentric relative to the interior space of the compression transmission device.
Figure 16:
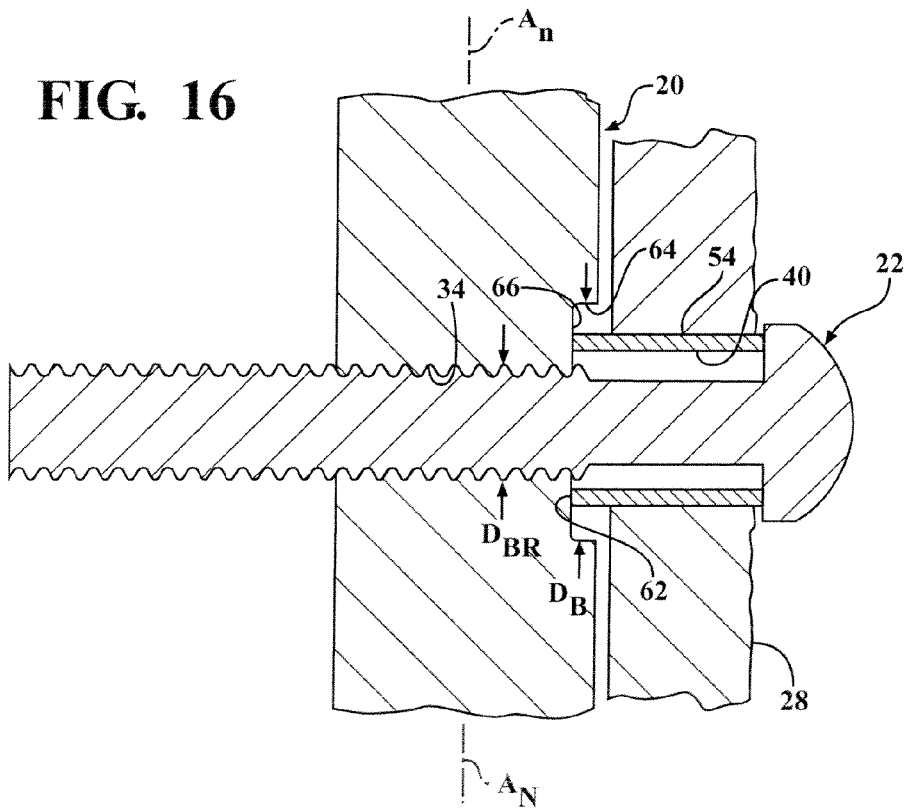
FIG. 16 is a cross-sectional view of the fastener extending through the compression transmission device and threadedly engaging the intramedullary nail along the bore when the cortex includes no far cortex hole and when the intramedullary nail includes a counterbore surface.
Figure 17:
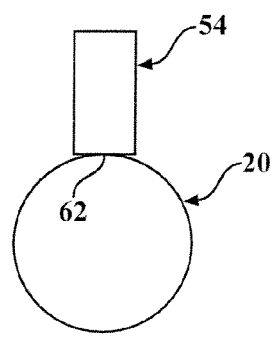
FIG. 17 is a cross-sectional view of the fastener, intramedullary nail and compression transmission device of FIG. 16 when the fastener also threadedly engages the cortex along the far cortex hole.
Figure 17:
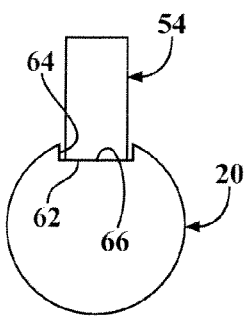
Figure 17:
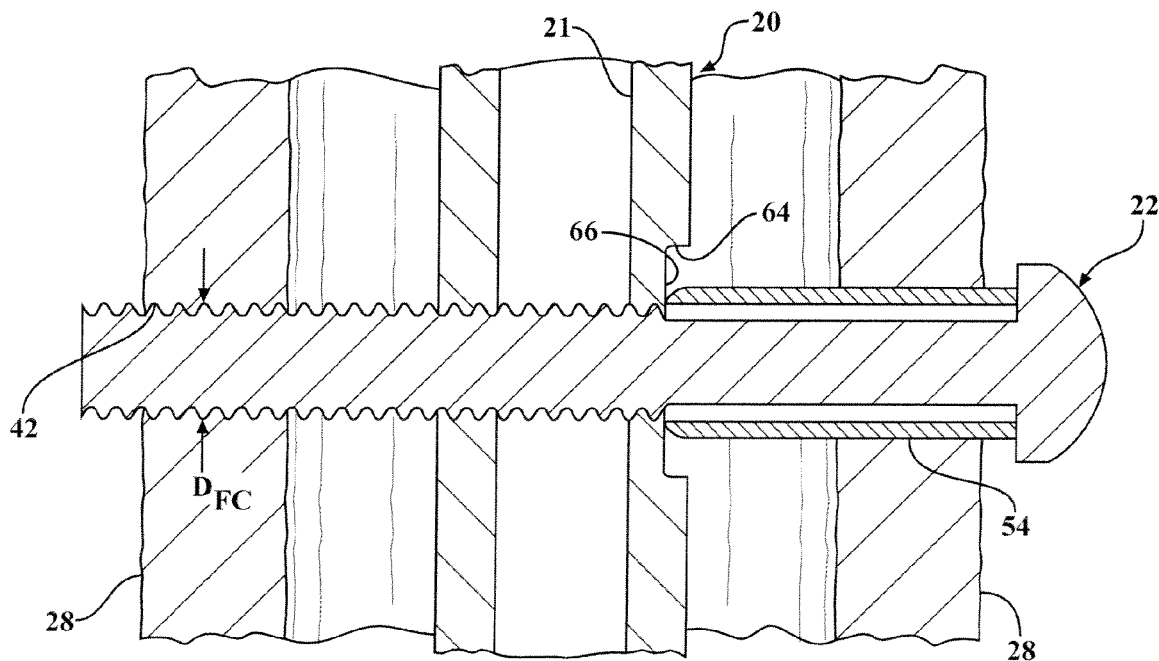
Figure 17A:
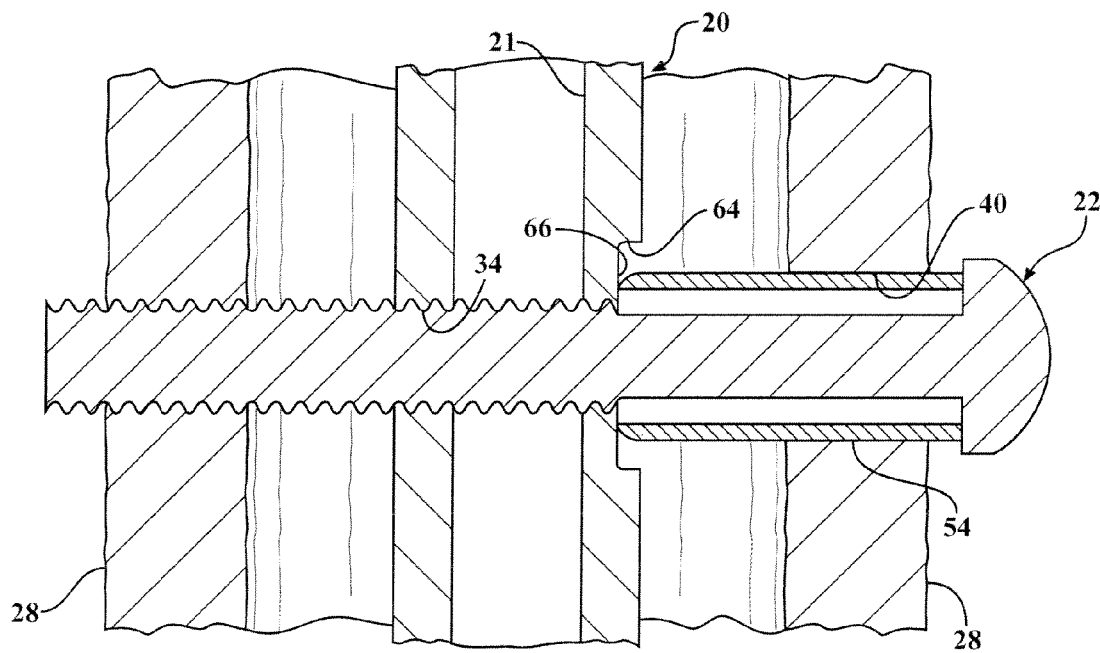
FIGS. 17A and 17B are cross-sectional views of the fastener, intramedullary nail and compression transmission device of FIG. 17 when the near cortex hole and bore are misaligned.
Figure 17B:
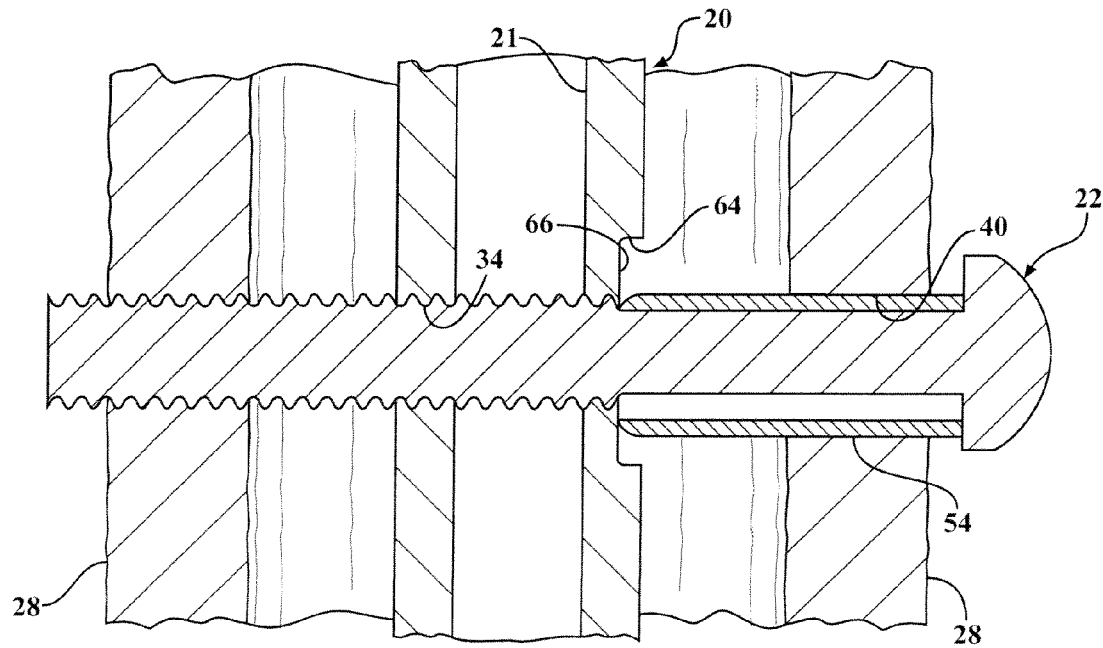

The nail-fastener apparatus includes the intramedullary nail 20 for insertion into a bone 24 having a bone diameter $D_{BN}$ and including a medullary canal 26 surrounded by a cortex 28. The intramedullary nail 20, generally indicated, extends longitudinally in the medullary canal 26 of the bone 24 along a nail axis $A_n$ between a top end 30 and a bottom end 32 thereof. The intramedullary nail 20 can be solid between the top end and the bottom end 32, as shown in FIGS. 5, 6, and 16. Alternatively, the intramedullary nail 20 can present a hollow opening 21 between the top end and the bottom end 32, as shown in FIGS. 17-17b. The intramedullary nail 20 also defines a bore 34 disposed transverse to, i.e., extending across but is not necessarily perpendicular to, the nail axis $A_n$ of the intramedullary nail 20. For example, the bore 34 can extend at various angles relative to the nail axis $A_n$. The intramedullary nail 20 may be straight, have an acute sharp bend, be bowed, or spiraled. The bore 34 is threaded and has a bore axis $A_b$ extending between the near opening 36 and the far opening 38 transverse to the intramedullary nail 20. The bore 34 has a bore diameter $D_{BR}$ including a central bore diameter $D_{CBR}$ disposed centrally between the near opening 36 and the far opening 38 of the bore 34. The intramedullary nail 20 may define a plurality of bores 34 as needed.

According to one embodiment of the invention, the cortex 28 of the bone 24, generally indicated, includes a near cortex hole 40 and a far cortex hole 42 both radially overlapping the bore 34. However, in certain situations, the cortex 28 may include only one of the cortex holes 40, 42. The near cortex hole 40 and the far cortex hole 42 may be located anywhere along the cortex 28. The teen "near cortex hole 40" refers to a hole extending along a compression portion 48 of the threaded fastener 22 or along a compression transmission device 54. The term "far cortex hole 42" refers to a hole extending along a threaded portion 50 of the threaded fastener 22 or a hole disposed between the compression transmission device 54 and an end 46 of the threaded fastener 22.

The near cortex hole 40 has a near cortex hole diameter $D_{NC}$ and the far cortex hole 42 has a far cortex hole diameter $D_{FC}$, the near cortex hole diameter $D_{NC}$ being greater than the far cortex hole diameter $D_{FC}$ and the far cortex hole diameter $D_{FC}$ being equal to the central bore diameter $D_{CBR}$ in the preferred embodiment, as illustrated. However, it may be appreciated that the far cortex hole diameter $D_{FC}$ may be unequal to the central bore diameter $D_{CBR}$. The near cortex hole diameter $D_{NC}$ can be coaxial with the central bore diameter $D_{CBR}$, or skewed and offset in relation to the central bore diameter $D_{CBR}$. The far cortex hole 42 can be coaxial with the central bore diameter $D_{CBR}$, or skewed in relation to the central bore diameter $D_{CBR}$.

Figure 12:
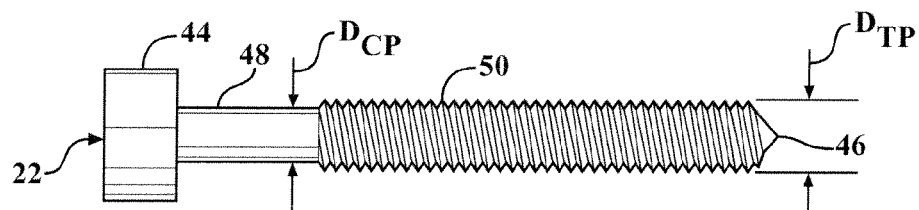
FIG. 12 is a side view of the fastener with the compression portion being unthreaded between the head and the threaded portion.
Figure 13:
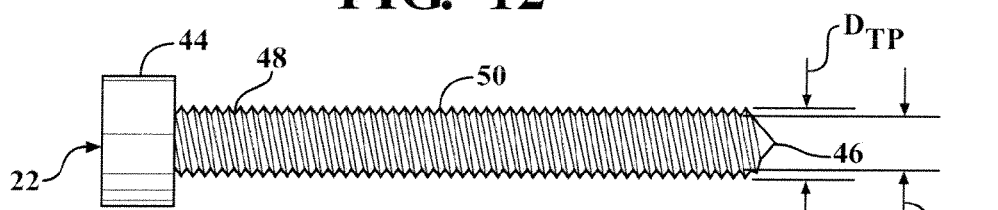
FIG. 13 is a side view of the fastener with the compression portion having threads continuing into the threaded portion.
Figure 14:
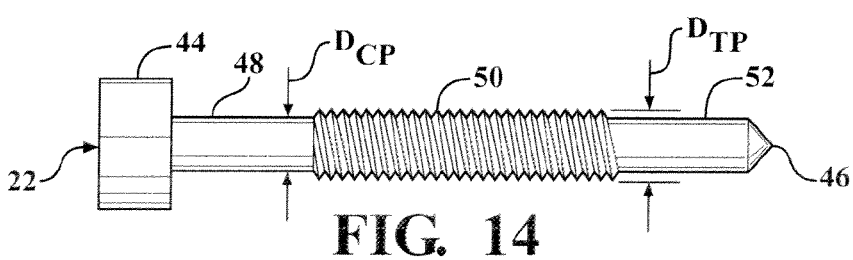
FIG. 14 is a side view of a centrally threaded fastener.

The threaded fastener 22, generally indicated, includes a head 44 and the end 46 with the compression portion 48 and the threaded portion 50 extending along a fastener axis A therebetween. The compression portion 48 of the threaded fastener 22 has a compression portion diameter $D_{CP}$ and the threaded portion 50 of the threaded fastener 22 has a threaded portion diameter $D_{TP}$. The compression portion diameter $D_{CP}$ may be smaller than or equal to the threaded portion diameter $D_{TP}$. The threaded portion diameter $D_{TP}$ is equal to the far cortex hole diameter $D_{FC}$ and the central bore diameter $D_{CBR}$ in the preferred embodiment, as illustrated, although it may be appreciated that the threaded portion diameter $D_{TP}$ may be unequal to the far cortex hole diameter $D_{FC}$ and the central bore diameter $D_{CBR}$. As shown in FIGS. 12 and 14, the compression portion 48 of the fastener 22 may be unthreaded between the head 44 and the threaded portion 50. As shown in FIG. 13, the compression portion 48 of the fastener 22 may be threaded with threads continuing into the threaded portion 50. As shown in FIG. 14, the fastener 22 can also include a compression portion 48 that is unthreaded and a second unthreaded portion 52 adjacent to the end 46, i.e., a centrally threaded fastener 22, which would eliminate thread purchase with the far cortex hole 42 and improve ease of fastener 22 removal. A plurality of threaded fasteners 22 at various orientations may be utilized as needed. Providing a threaded fastener 22 with a threaded portion diameter $D_{TP}$ being equal to the central bore diameter $D_{CBR}$ results in a highly stable construct free of toggle. The enlarged near cortex hole 40 eliminates binding during fastener 22 insertion.

The threaded fastener 22 extends through the compression transmission device 54 and the intramedullary nail 20 so as to extend transversely to the intramedullary nail 20 for threadedly engaging the bore 34 and fixating the intramedullary nail 20 within the medullary canal 26. In one embodiment, the threaded fastener 22 also extends through the far cortex hole 42. The compression transmission device 54 typically contacts the near cortex hole 40 for preventing movement of the compression transmission device 54 relative to the near cortex hole 40.

The compression transmission device 54, generally indicated, includes an exterior 56 having an exterior diameter $D_E$ and an interior 58 having an interior diameter $D_I$ defining an interior space. The exterior diameter $D_E$ of the compression transmission device 54 should be carefully considered to allow for a sufficient fastener 22 diameter for sufficient mechanical strength, but be small enough so that the bone 24 is not excessively weakened.

Figure 7A:
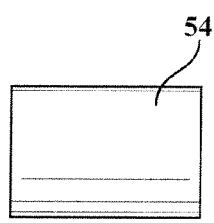
FIG. 7A is a side view of the compression transmission device.
Figure 7B:
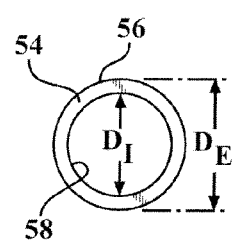
FIG. 7B is an end view of FIG. 7A.
Figure 8A:
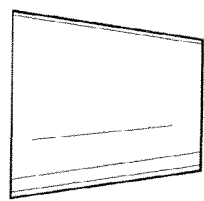
FIG. 8A is a side view of an alternative compression transmission device design.
Figure 8B:
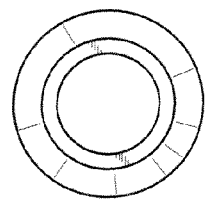
FIG. 8B is an end view of FIG. 8B.
Figure 9A:
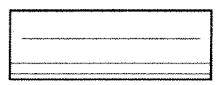
FIG. 9A is a side view of an alternative compression transmission device design.
Figure 9B:
FIG. 9B is an end view of FIG. 9A.
Figure 10A:
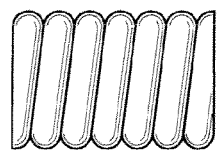
FIG. 10A is a side view of an alternative compression transmission device design.
Figure 10B:
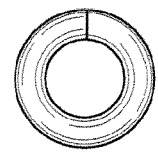
FIG. 10B is an end view of FIG. 10A.
Figure 11A:
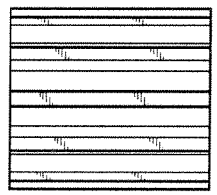
FIG. 11A is a side view of an alternative compression transmission device design.
Figure 11B:
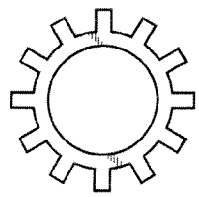
FIG. 11B is an end view of FIG. 11A.

The compression transmission device 54 can have a circular or non-circular cross section, and may be comprised of a single or a plurality of parts. As shown in the compression transmission device 54 design examples in FIGS. 7A-11B, though not exhaustive, the device can include straight or tapered sides as shown in FIGS. 7A-8B, a smooth exterior surface or an exterior surface with protrusions as shown in FIGS. 7B and 11B, a semi-circular cross section as shown in FIG. 9A, and be comprised of a spring or helical coil as shown in FIGS. 10A and 10B. The compression transmission device 54 could also include partially tapered sides, a flange on one or both ends, a narrowed central diameter, an expanded central diameter (barrel shaped), and threads on the interior and/or exterior surface. The device can also be comprised of mesh, a plurality of cylindrical discs, of two parts each having a semi-circular cross section, or of a single piece having a partially circular cross section. Further, the device can be perforated, ribbed or corrugated, resorbable, expandable, or drug eluting. All compression transmission devices 54 shroud the fastener 22, thus preventing osseointegration onto the fastener 22. This allows for ease of fastener 22 removal in cases of hardware explantation. Further, the compression transmission devices 54 which are elastic, or store energy, will return to their uncompressed shapes as fastener 22 removal is initiated. This will aid in the removal of bony integration, and ultimately in the removal of all hardware.

The compression transmission device 54 transmits the compressional load of the threaded fastener 22 to the intramedullary nail 20 during fixation, rather than relying on fastener 22 to bone 24 purchase for fixation. Thus, this device can be used in patients with poor bone quality (e.g., secondary to osteoporosis, diabetes, etc.), with unstable fractures (e.g., secondary to complex fractures, exceptionally high or low fractures that traditionally would not be treated with intramedullary nailing, etc.), with only one stable cortex 28 (complex fractures, tumor resections, etc.), or with limited intramedullary contact as would occur in unreamed nailing. The use of the compression transmission device 54 with the fastener 22 improves the tactile sensation experienced by the surgeon as the fastener 22 is installed into the intramedullary nail 20 because the surgeon will feel a hard stop as the head 44 of the fastener 22 and nail 20 compress the compression transmission device 54.

Figure 1:
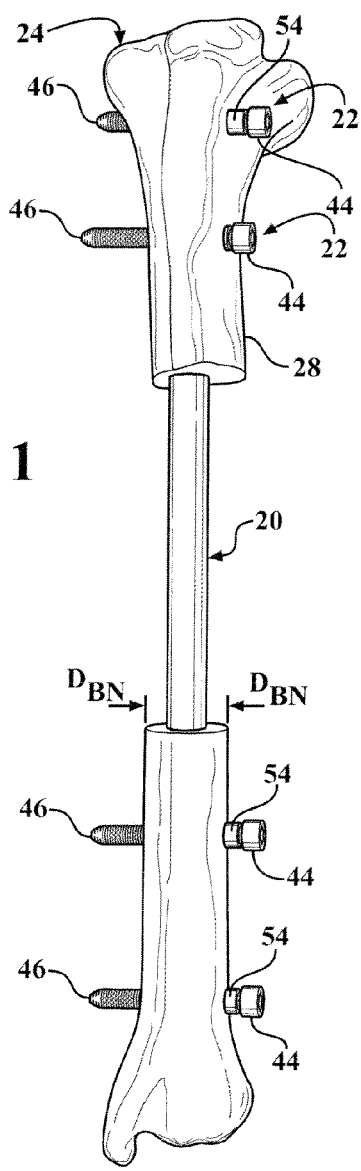
FIG. 1 is a side perspective view showing the nail-fastener of the subject invention.
Figure 2:
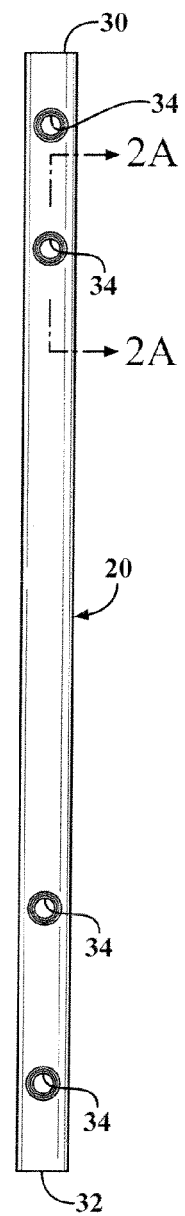
FIG. 2 is a front view of the bores disposed in the intramedullary nail.
Figure 3:
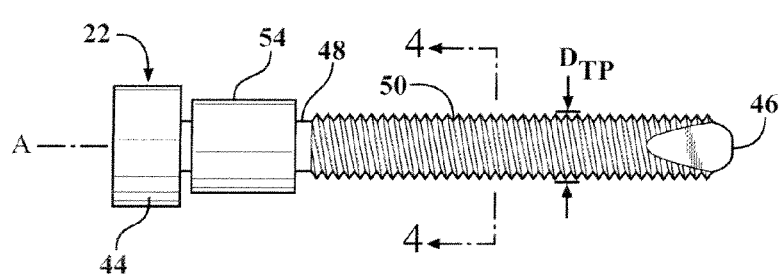
FIG. 3 is a side view of a fastener extending through the compression transmission device.
Figure 4:
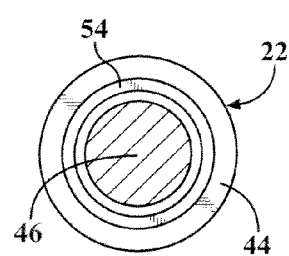
FIG. 4 is a cross-sectional view taken along line 4 of FIG. 3.
Figure 2A:
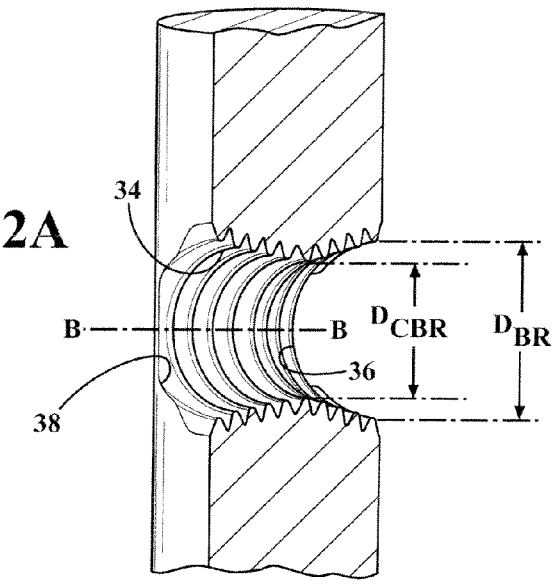
FIG. 2A is a sectional perspective view taken along line 2A-2A of FIG. 2.
Figure 26:
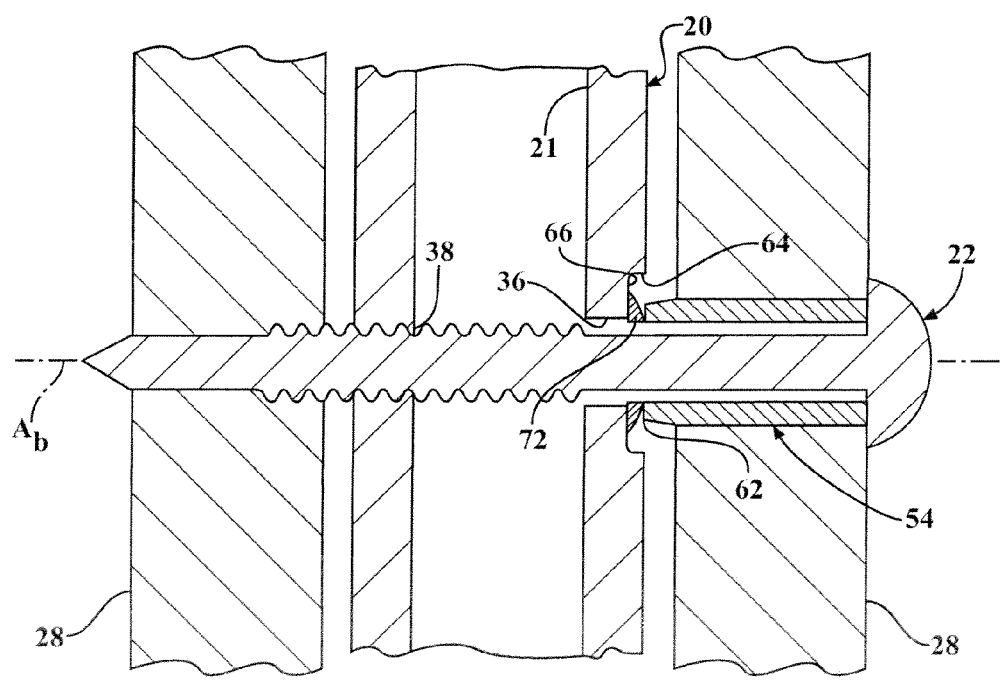
FIG. 26 is a cross-section view of the nail-fastener apparatus according to another embodiment of the invention.

In one embodiment, as shown in FIG. 2A, the bore diameter $D_{BR}$ increases from the central bore diameter $D_{CBR}$ to the near opening 36 and from the central bore diameter $D_{CBR}$ to the far opening 38 for allowing the fastener axis A to be skewed relative to the bore axis $A_b$ while remaining threadedly engaged. This facilitates fastener 22 installation by allowing for more room for error by the surgeon as the fastener 22 will insert and threadedly engage the bore 34 even if the fastener axis A is not parallel to the bore axis $A_b$. The diameter of the bore 34 could vary in other ways, and the narrowest diameter of the bore 34 could be located elsewhere along the intramedullary nail 20, instead of at the central bore diameter $D_{CBR}$. For example, the narrowest diameter of the bore 34 could be located adjacent the near opening 36 or adjacent the far opening 38 of the intramedullary nail 20, as shown in FIG. 26. In another embodiment, the bore diameter $D_{BR}$ can be consistent from the central bore diameter $D_{CBR}$ to the near opening 36 and from the central bore diameter $D_{CBR}$ to the far opening 38.

The interior space of the compression transmission device 54 is greater than the compression portion diameter $D_{CP}$ of the fastener 22 for providing space at least partially about the threaded fastener 22 for allowing the fastener axis A to be variously disposed, i.e., concentric, eccentric, and/or skewed, relative to the interior space. Thus, the compression transmission device 54 is independent of the fastener 22, i.e., there is no interdigitation of the compression transmission device 54 and the fastener 22. A fastener 22 with a compression portion 48 having a compression portion diameter $D_{CP}$ being smaller than the threaded portion diameter $D_{TP}$ allows for the use of a compression transmission device 54 having a smaller interior 58 space while still allowing the fastener axis A to be disposed eccentrically relative to the interior space. Allowing the fastener axis A to be variously disposed relative to the interior space of the compression transmission device 54 and the bore axis $A_b$ improves ease of installation of the fastener 22 in the intramedullary nail 20, resulting in faster surgical procedures. This results in a decrease in radiation exposure due to successful fastener 22 implantation on initial attempts. The compression transmission device 54 maintains a fixed predetermined angle relationship between the fastener 22 and the intramedullary nail 20 once installed and compressed, minimizing micro-movements of the nail 20.

Figure 15:
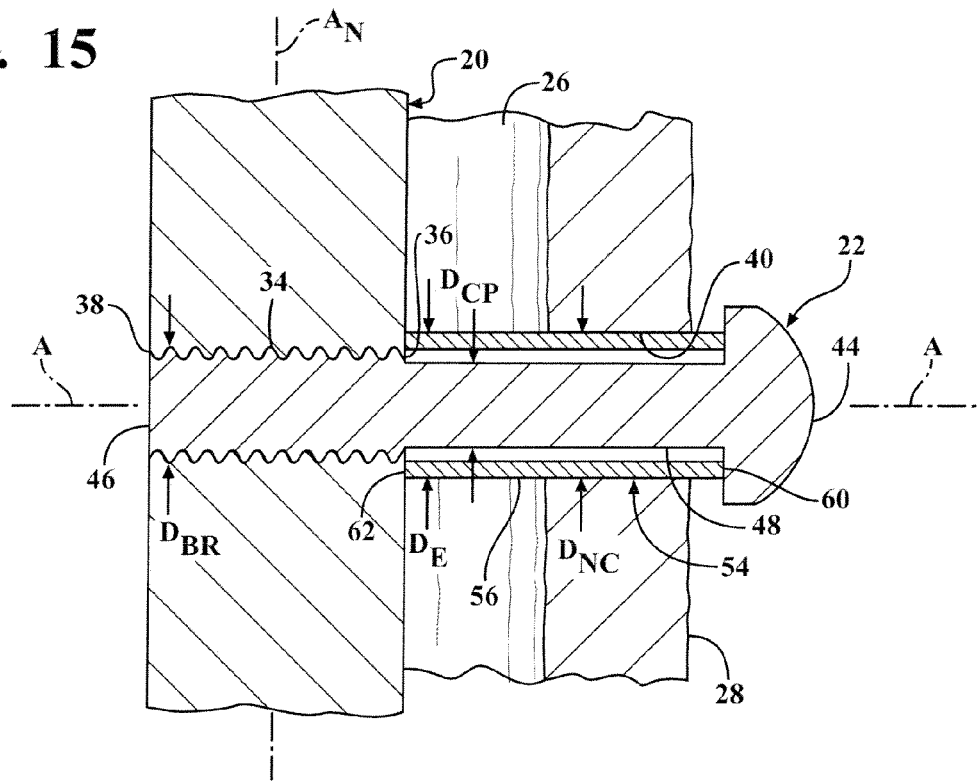
FIG. 15 is a cross-sectional view of the fastener extending through the compression transmission device and threadedly engaging the intramedullary nail along the bore when the cortex includes no far cortex hole.

According to another embodiment of the invention, the threaded fastener 22 only extends through the near cortex hole 40 and the bore 34 of the intramedullary nail 20, as shown in FIG. 15, and does not extend through the far cortex hole 42. This embodiment may be used when a portion of the patient's cortex 28 is missing, for example due to tumor resection. In this situation, there may be enough cortex 28 to form the near cortex hole 40, but not enough to form the far cortex hole 42. This embodiment may also be used when a portion of the cortex 28 is unstable, for example due to trauma, in which case there is enough cortex 28 to form the far cortex holes 40, 42, but it is only desirable to form the near cortex hole 40.

The nail-fastener apparatus of FIG. 15 also includes the intramedullary nail 20 defining the bore 34. The threaded fastener 22 includes the head 44 and the end 46 with the threaded portion 50 extending along the fastener axis A therebetween. The threaded portion 50 extends through the near cortex hole 40 of the bone 24 and threadedly engages the intramedullary nail 20 along the cortex 28. The threaded fastener 22 of FIG. 15 also includes the compression portion 48 presenting the compression portion diameter $D_{CP}$ and extending along the fastener axis A between the threaded portion 50 and the head 44. The compression transmission device 54 extends through the near cortex hole 40 and surrounds the compression portion 48 of the threaded fastener 22. The compression transmission device 54 also has the exterior 56 and the interior 58 defining the interior space. The compression transmission device 54 is disposed between the head 44 of the threaded fastener 22 and the intramedullary nail 20. More specifically, the compression transmission device 54 extends from a device top end 60 to a device bottom end 62, the device top end 60 engages the head 44 of the fastener 22, and the device bottom end 62 engages the intramedullary nail 20 adjacent to and around the near opening 36 of the bore 34. The interior space is greater than the compression portion diameter $D_{CP}$ of the fastener 22 for providing space at least partially about the threaded fastener 22 and thus allowing the fastener axis A to be variously disposed relative to the interior space.

The threaded portion 50 of the threaded fastener 22 of FIG. 15 includes threads, and the compression portion 48 does not include threads. In an alternate embodiment, the compression portion 48 could also include threads such that the threaded fastener 22 would be threaded continuously from the head 44 to the end 46. The end 46 threaded fastener 22 of FIG. 15 is aligned with an exterior surface of the intramedullary nail 20, but alternatively could extend past the exterior surface outwardly of the intramedullary nail 20, or could be disposed in the bore 34 of the intramedullary nail 20.

FIG. 15 also shows that the bore 34 of the intramedullary nail 20 is threaded and presents the bore diameter $D_{BR}$ extending between the near opening 36 and the far opening 38. In the embodiment of FIG. 15, the bore diameter $D_{BR}$ is consistent from the near opening 36 to the far opening 38. However, the bore diameter $D_{BR}$ may vary between the near opening 36 and the far opening 38, as shown in FIG. 5.

Figure 23:
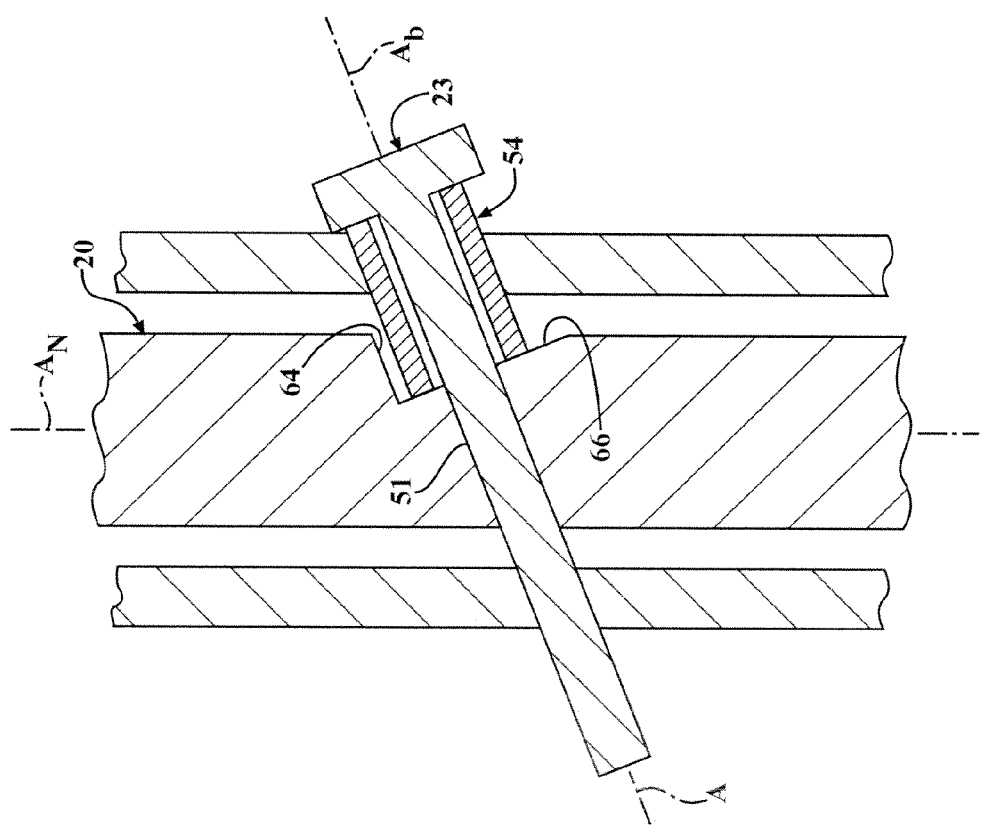
FIG. 23 is a cross-sectional view of the nail-fastener apparatus wherein an unthreaded fastener is disposed at an angle relative to the intramedullary nail and the intramedullary nail includes the counterbore surface.

According to another embodiment of the invention, the exterior surface of the intramedullary nail 20 presents a counterbore surface 64, as shown in FIGS. 16-21. In the embodiment of FIG. 16, the counterbore surface 64 extends from the exterior surface to a base surface 66. The counterbore surface 64 typically extends perpendicular to the center nail axis $A_n$ and parallel to the bore axis $A_b$ or fastener axis A. The base surface 66 presents a base diameter $D_b$ surrounding the bore 34. The base diameter $D_b$ is greater than the bore diameter $D_{BR}$, and the device bottom end 62 of the compression transmission device 54 engages the base surface 66. FIG. 16 shows an embodiment wherein the threaded fastener 22 extends perpendicular to the intramedullary nail 20 and the intramedullary nail 20 includes a counterbore surface 64 extending perpendicular to the exterior surface and having a consistent depth surrounding the bore 34. In the embodiment of FIG. 16, the base surface 66 extends parallel to the center nail axis $A_n$ and perpendicular to the fastener axis A. FIG. 17 shows the counterbore surface 64 when the cortex 28 includes the near cortex hole 40 and the far cortex hole 42, and when the near cortex hole 40 and the bore 34 of the intramedullary nail 20 are aligned. In this embodiment, or any embodiment wherein the cortex 28 provides a far cortex hole 42, the bore 34 of the intramedullary nail 20 could be provided without threads, and the threaded portion 50 of the threaded fastener 22 would be threaded into the cortex 28 along the far cortex hole 42. FIG. 23 shows an alternate embodiment wherein the fastener 22 is disposed at an angle relative to the intramedullary nail 20. In the embodiment of FIG. 23, the counterbore surface 64 also extends at an angle relative to the exterior surface and has a depth that varies around the bore 34. In this embodiment, the base surface 66 also extends at an angle relative to the center nail axis $A_n$ and perpendicular to the fastener axis A, and the base surface 66 transitions into the exterior surface along one side of the counterbore.

As shown in FIG. 16A, the counterbore surface 64 provides a flat surface to support the device bottom end 62 of the compression transmission device 54 and thus provides additional stability, compared to the embodiment of FIGS. 15 and 15A without the counterbore surface 64. The device bottom end 62 of the compression transmission device 54 can be disposed at various radial positions relative to the bore 34 of the intramedullary nail 20 without resistance. If the near cortex hole 40 and the bore 34 of the intramedullary nail 20 are misaligned, it may be difficult to insert the threaded fastener 22 into the intramedullary nail 20 and thus surgery may be delayed. However, when the counterbore surface 64 is provided, a surgeon can quickly determine the proper placement of the compression transmission device 54 and near cortex hole 40 relative to the intramedullary nail 20. FIGS. 17A and 17B each show an example of the threaded fastener 22 securely maintained relative to the intramedullary nail 20 when the near cortex hole 40 and the bore 34 of the intramedullary nail 20 are misaligned.

Figure 18:
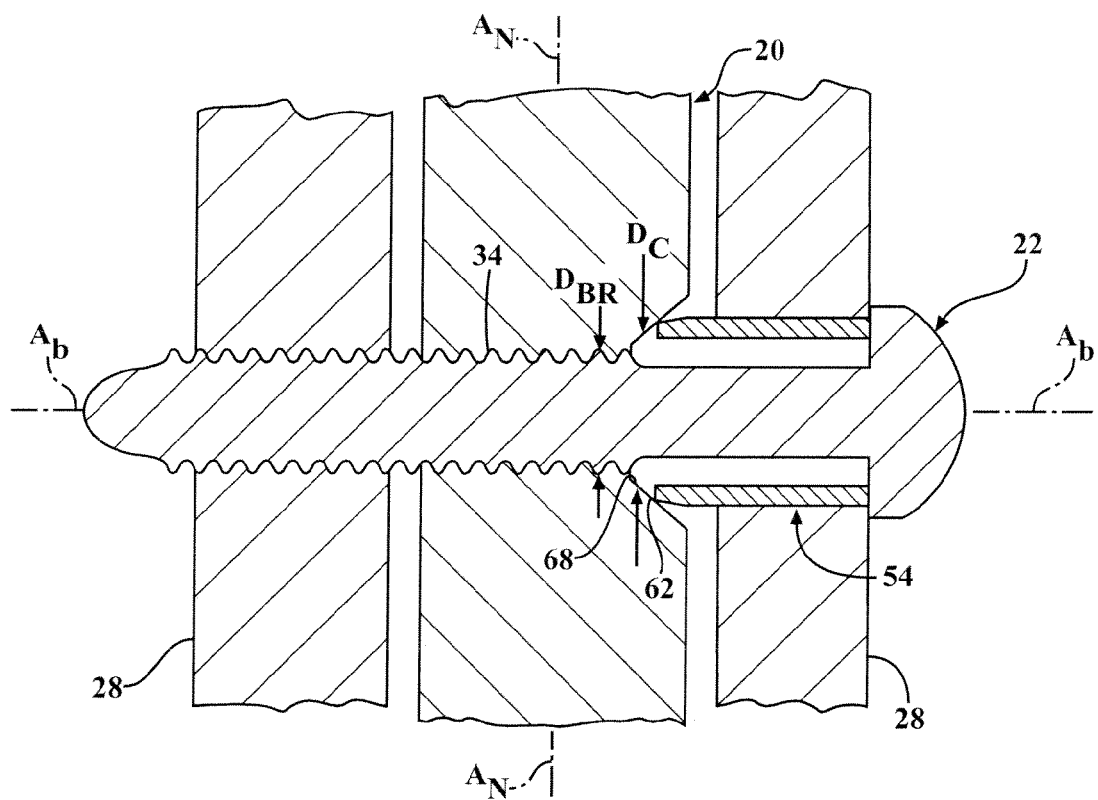
FIG. 18 is a cross-sectional view of the fastener extending through the compression transmission device and threadedly engaging the intramedullary nail along the bore and the cortex along the far cortex hole when the intramedullary nail includes a countersink surface.

FIG. 18 illustrates another embodiment of the invention, wherein the exterior surface of the intramedullary nail 20 presents a countersink surface 68. The countersink surface 68 extends from the exterior surface to the bore 34. The countersink surface 68 also extends at an angle relative to the bore axis $A_b$ and to the center nail axis $A_n$. The countersink surface 68 has a countersink diameter $D_c$ which is greater than the bore diameter $D_{BR}$. The device bottom end 62 of the compression transmission device 54 contacts the countersink surface 68, and the countersink surface 68 centers the threaded fastener 22 along the bore axis $A_b$ of the intramedullary nail 20. In contrast, the counterbore surface 64 allows the device bottom end 62 of the compression transmission device 54 to simply sit on the base surface 66 and is not influenced or centered by a countersink surface 68.

Figure 19:
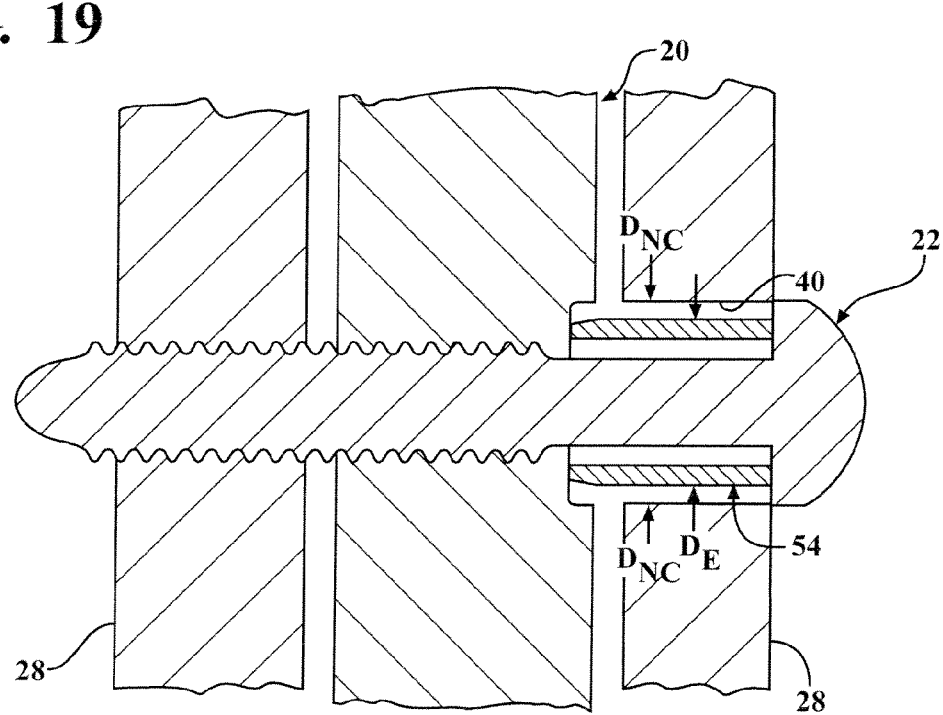
FIG. 19 is a cross-sectional view of the fastener extending through the compression transmission device and threadedly engaging the intramedullary nail along the bore and the cortex along the far cortex hole when the exterior diameter of the compression transmission collar is less than the near cortex hole diameter.

In the embodiments of FIGS. 5, 6, and 15-18, the exterior diameter $D_E$ of the compression transmission device 54 is equal to the near cortex hole diameter $D_{NC}$ such that the exterior 56 of the compression transmission device 54 engages the cortex 28 along the near cortex hole 40. However, in an alternate embodiment, shown in FIG. 19, the exterior diameter $D_E$ of the compression transmission device 54 is less than the near cortex hole diameter $D_{NC}$ such that the compression transmission device 54 and the cortex 28 provide a space therebetween. As shown in FIG. 19, the space is greater than the exterior diameter $D_E$ of the compression transmission device 54. This embodiment may be used to enhance bone growth across the near cortex hole 40 during early stages of recovery. As the cortex 28 grows, it will eventually surround the compression transmission device 54 and increase construct rigidity. This embodiment will allow for a dynamic evolving construct rigidity that can be tuned to enhance bone growth across a fracture for the duration of healing.

The stiffness of the nail-fastener apparatus can be adjusted by adjusting the size of the near cortex hole diameter $D_{NC}$, or the distance between the cortex 28 and the exterior diameter $D_E$ of the compression transmission device 54. In alternate embodiment, the compression transmission device 54 and threaded fastener 22 of FIG. 19 can be welded together along the device top end 60 and the head 44, or the compression transmission device 54 and threaded fastener 22 can be provided as an integral unit.

Figure 20:
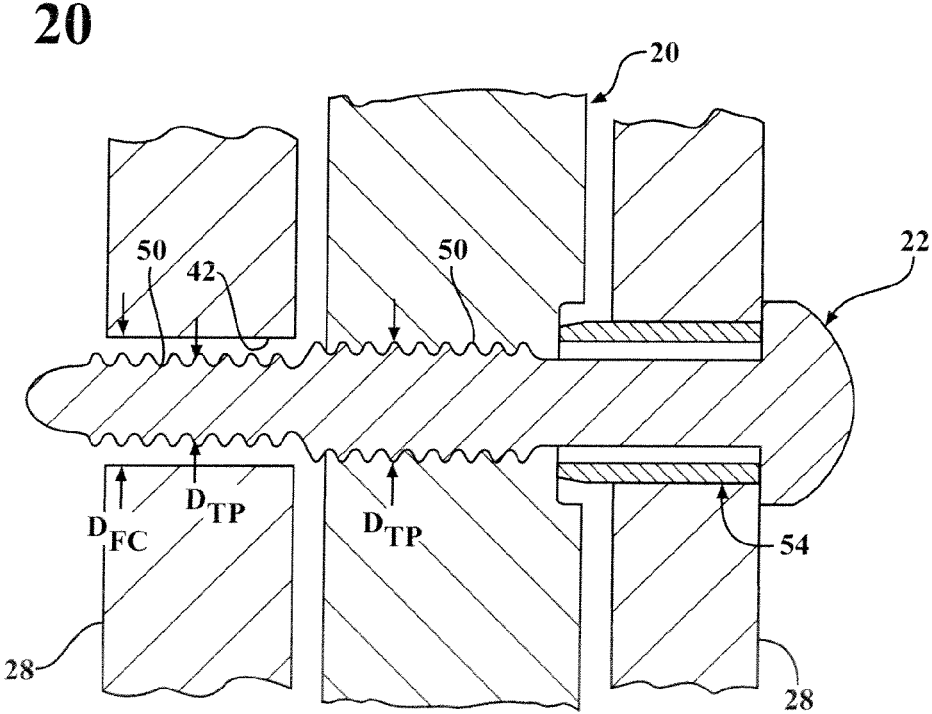
FIG. 20 is a cross-sectional view of the fastener extending through the compression transmission device and threadedly engaging the intramedullary nail along the bore and extending through the far cortex hole when the threaded portion diameter of the threaded fastener is less than the far cortex hole diameter.

In yet another embodiment, as shown in FIG. 20, the threaded portion 50 of the threaded fastener 22 extends into the far cortex hole 42, and the threaded portion diameter $D_{TP}$ along the far cortex hole 42 is less than the far cortex hole diameter $D_{FC}$ such that the threaded fastener 22 and the cortex 28 provide a space therebetween. This embodiment may be used to enhance bone growth across the far cortex hole 42 during early stages of recovery. The threaded portion diameter $D_{TP}$ of the threaded fastener 22 along the bore 34 of the intramedullary nail 20 can be greater than the threaded portion diameter $D_{TP}$ along the far cortex hole 42, which is also shown in FIG. 20. As the cortex 28 grows, it will eventually surround the threaded portion 50 and increase construct rigidity. This embodiment will also allow for a dynamic evolving construct rigidity that can be tuned to enhance bone growth across a fracture for the duration of healing.

Figure 21:
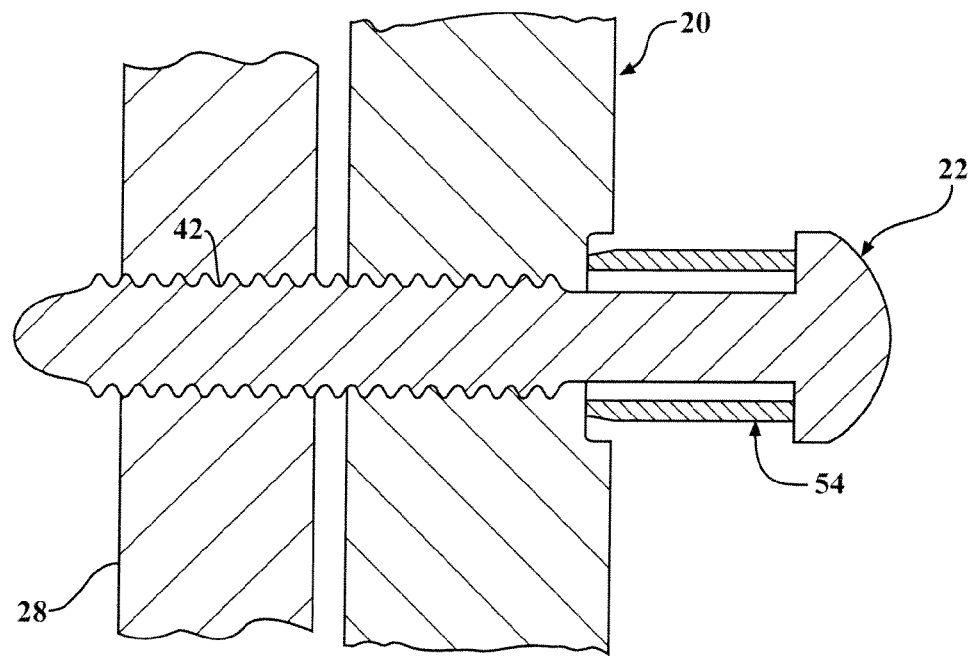
FIG. 21 is a cross-sectional view of the fastener extending through the compression transmission device and threadedly engaging the intramedullary nail along the bore and the cortex along the far cortex hole when the cortex includes no near cortex hole.

In the situations where a portion of the cortex 28 is missing or unstable, for example due to trauma or tumor resection, the bone 24 may include enough cortex 28 to form the far cortex hole 42, but not the near cortex hole 40, as shown in FIG. 21. In this embodiment, the threaded fastener 22 extends through the intramedullary nail 20 and threadedly engages the cortex 28 along the far cortex hole 42.

Figure 24A:
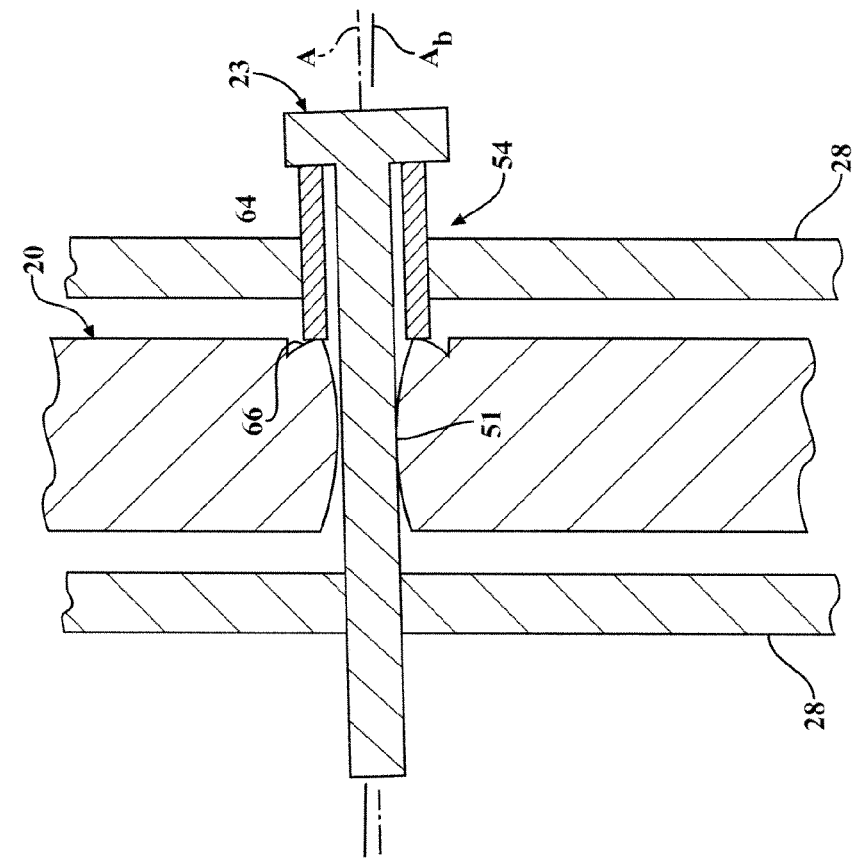
FIGS. 24A-24C are cross-sectional views of the unthreaded fastener, intramedullary nail and compression transmission device wherein a base surface of the counterbore is convex.
Figure 24C:
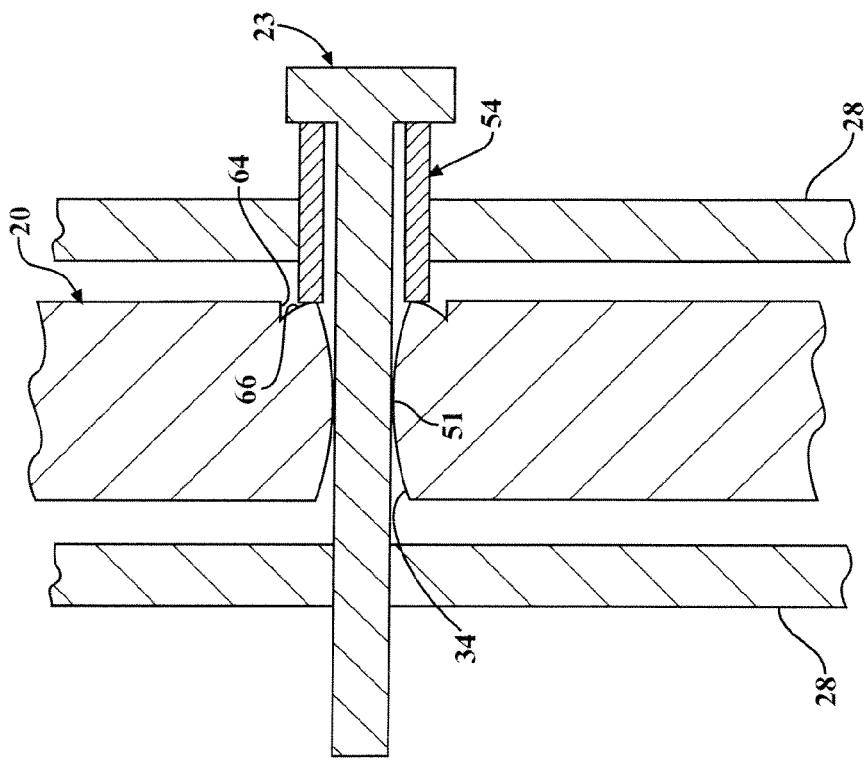
Figure 24B:
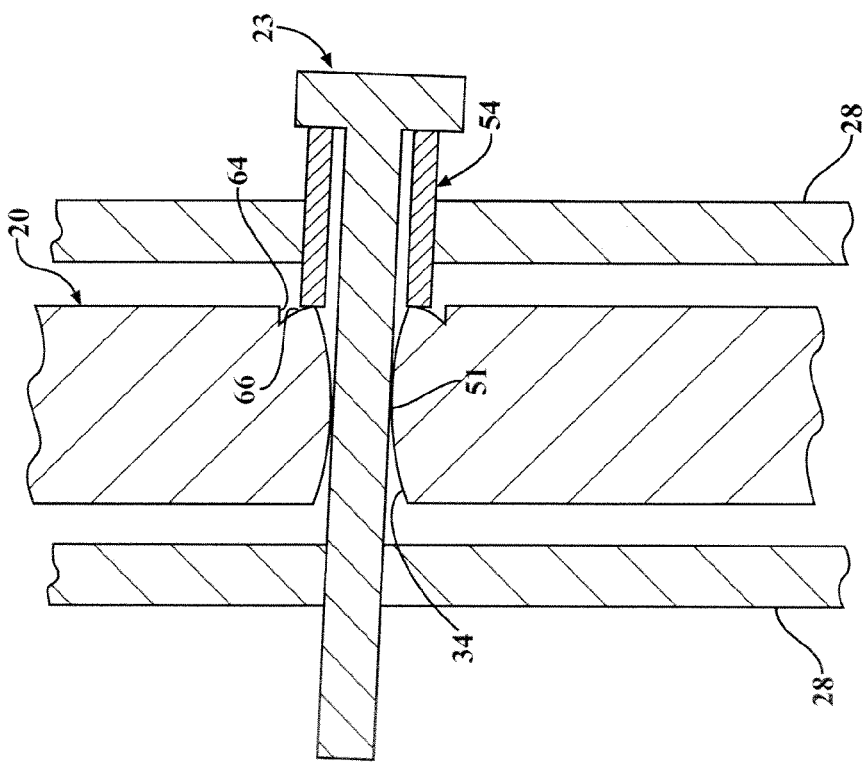

FIGS. 24A-24C illustrate another alternate embodiment wherein the base surface 66 of the counterbore is convex and presents a curved shape similar to a flattened hemisphere or a button. In this embodiment, the device bottom end 62 of the compression transmission device 54 engages the convex base surface 66. The convex surface allows the compression transmission device 54 and threaded fastener 22 to be disposed at various angles relative to the bore axis $A_b$. The convex base surface 66 also tends to center to the compression transmission device 54 relative to the threaded fastener 22 and stabilizes the compression transmission device 54 by circumferential contact. The convex shape of the base surface 66 can be machined into the exterior surface of the intramedullary nail 20.

Figure 25B:
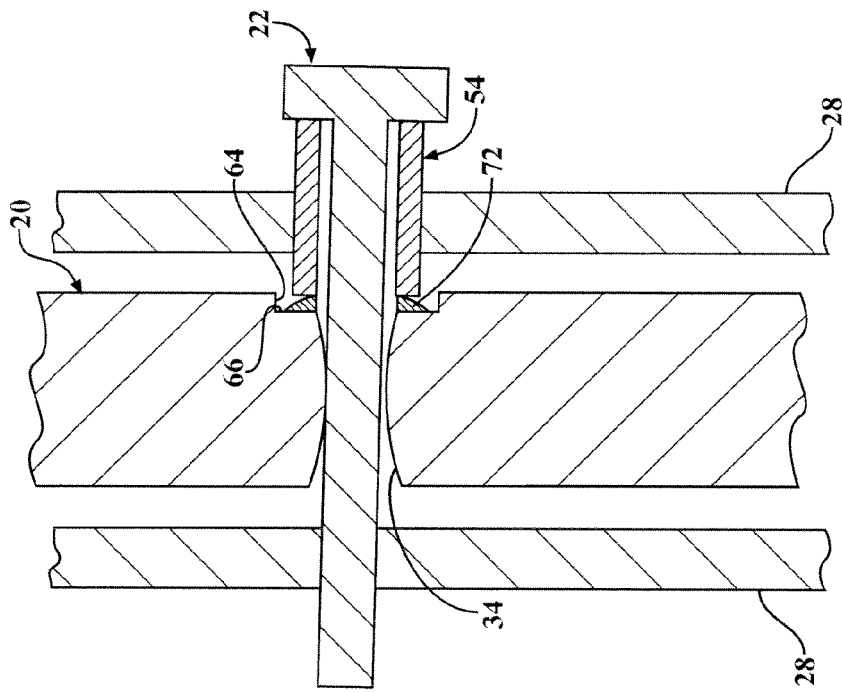
FIGS. 25A-25C are cross-sectional views of the unthreaded fastener, intramedullary nail and compression transmission device wherein a washer presenting a convex surface is disposed on the base surface of the counterbore.
Figure 25A:
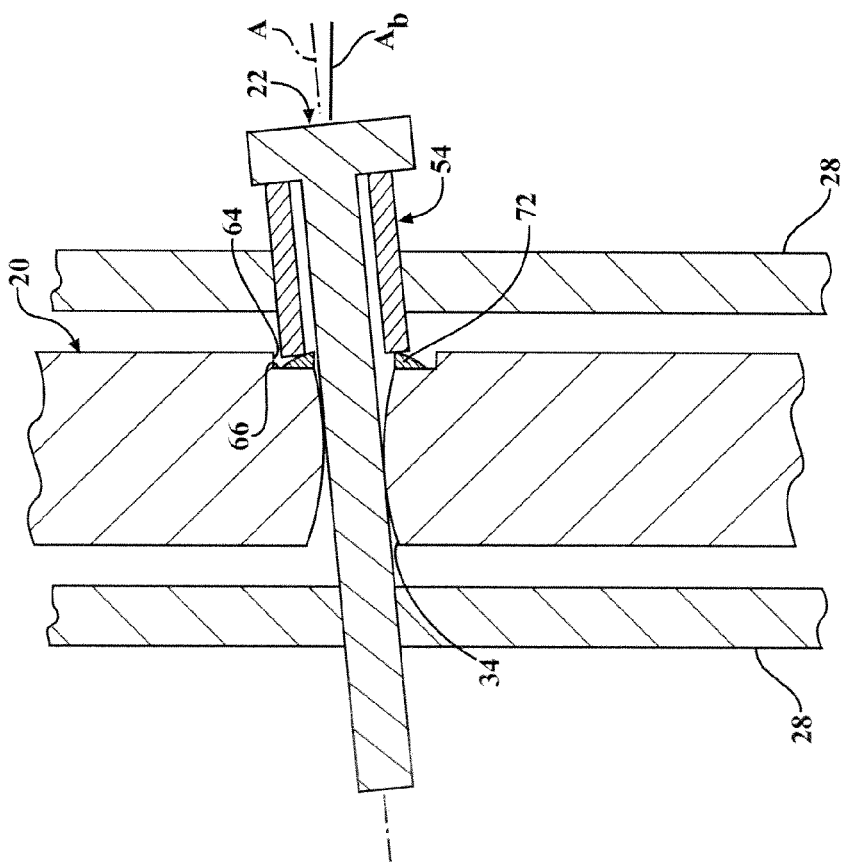
Figure 25C:
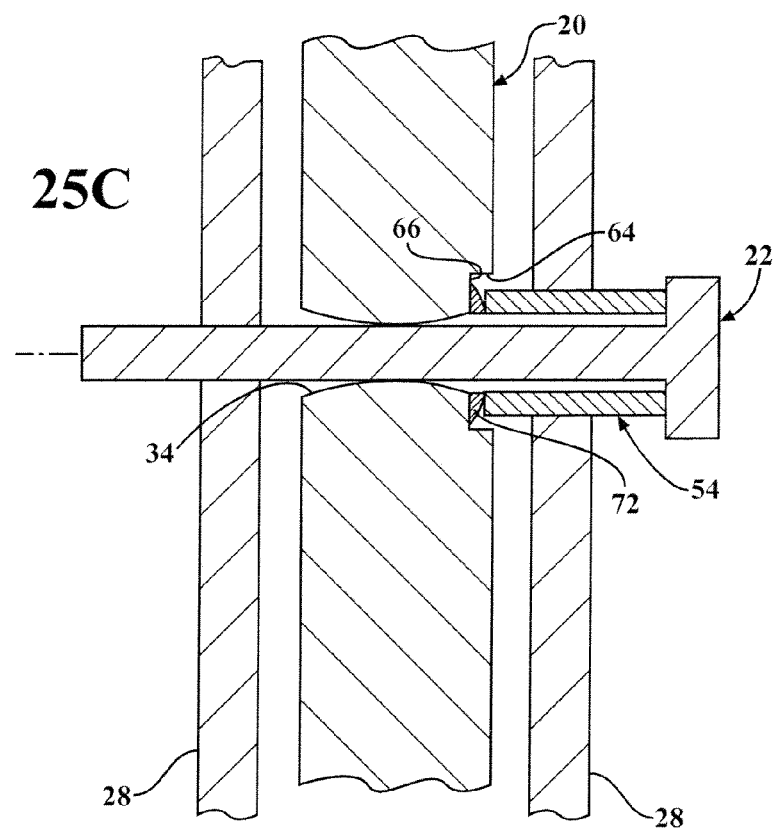

FIGS. 25A-25C illustrate another alternate embodiment wherein the intramedullary nail includes the counterbore surface 64 and base surface 66, as in the embodiments of FIGS. 15 and 17. However, in this embodiment, the convex surface is provided by a washer 72 disposed on the base surface 66, and the device bottom end 62 of the compression transmission device 54 engages the convex surface of the washer 72. The convex surface of the washer 72 allows the compression transmission device 54 and threaded fastener 22 to be disposed at various angles relative to the bore axis $A_b$, and facilitates rotational flexibility of the compression transmission device 54 and threaded fastener 22. The washer 72 also stabilizes the compression transmission device 54 by circumferential contact. Translational misalignment of the near cortex hole 40 and the bore 34 of the intramedullary nail 20, as shown in FIGS. 17A and 17B, is also facilitated by the washer 72.

According to another alternate embodiment, which is also shown in FIGS. 23-25, a fastener 23 is formed without threads and utilizes friction, rather than threads, to engage the bore of the intramedullary nail 20, the far cortex hole 42, or both. The friction or interference fit maintains the fastener 23 fixed in place relative to the cortex 28 and the intramedullary nail 22.

In this alternate embodiment, the unthreaded fastener 23 includes a first portion 51 extending between a head 44 and an end 46 for frictionally engaging the bore 34 of the intramedullary nail 20, instead of the threaded portion 50. The first portion 51 of the unthreaded fastener 22 could also frictionally engage the far cortex hole 42, instead of or in addition to the bore of the intramedullary nail 20.

FIG. 26 illustrates another preferred embodiment of the invention, wherein the intramedullary nail 20 presents a hollow opening 21. The intramedullary nail 20 also includes an unthreaded bore 34, and the diameter of the near opening 36 if the bore 34 is greater than the diameter of the far opening 38. The exterior surface of the intramedullary nail 20 presents the counterbore surface 64 and the washer 72 is disposed on the base surface 66 of the counterbore. The device bottom end 62 of the compression transmission 54 device engages the washer 72 and the threaded fastener 22 passes through the near opening 36 and taps the unthreaded far opening 38 of the intramedullary nail 20 and the adjacent cortex 28. This embodiment provides all six rotational and translational degrees of freedom and thus exceptional flexibility in the placement of the fastener 22 relative to the cortex 28 and the intramedullary nail 20. For example, the fastener 22 can be angled up to 10 degrees in all directions off the bore axis $A_b$ shown in FIG. 26.

The nail-fastener apparatus of the present invention provides several advantages over nail-fasteners of the prior art, such as the nail-fastener of Dell-Oca. One advantage is a greater amount of predictable precision by the surgeon. For example, the surgeon can determine with certainty the location of the end 46 of the threaded fastener 22 and the location of the device bottom end 62 of the compression transmission device 54. Additionally, the interior space provided by the compression transmission device 54 allows the fastener axis 22 to be disposed at various angles relative to the nail axis $A_b$.

The subject invention also includes a method for implanting an intramedullary nail 20 into a medullary canal 26 surrounded by a cortex 28 of a bone 24 having a bone diameter $D_{BN}$. In one embodiment, the method comprises the steps of creating a bore 34 with threads and having a bore axis $A_b$ extending between a near opening 36 and a far opening 38 transverse to the intramedullary nail 20, the bore 34 having a bore diameter $D_{BR}$ including a central bore diameter $D_{CBR}$ disposed centrally between the near opening 36 and the far opening 38 of the bore 34 in the intramedullary nail 20 wherein the bore diameter $D_{BR}$ increases from the central bore diameter $D_{CBR}$ to the near opening 36 and from the central bore diameter $D_{CBR}$ to the far opening 38 for allowing the fastener axis A to be skewed relative to the bore axis $A_b$ while remaining threadedly engaged.

The method may include using fluoroscopy or a targeting jig, locating the bore 34 and forming a near cortex hole 40 with a near cortex hole diameter $D_{NC}$ in the cortex 28 before using the nail 20 or jig as a guide to form a far cortex hole 42 with a far cortex hole diameter $D_{FC}$ in the cortex 28 preferably being equal, as illustrated, though it may be unequal, to the central bore diameter $D_{CBR}$ with both in radially overlapping relationship to the bore 34 and with the near cortex hole diameter $D_{NC}$ being greater than the far cortex hole diameter $D_{FC}$.

The method also includes providing a threaded fastener 22 including a head 44 and an end 46 with a compression portion 48 having a compression portion diameter $D_{CP}$ and a threaded portion 50 having a threaded portion diameter $D_{TP}$ extending along a fastener axis A therebetween, where the threaded portion diameter $D_{TP}$ is preferably equal, as illustrated, though it may be unequal, to the far cortex hole diameter $D_{FC}$ and the central bore diameter $D_{CBR}$. The method can further include providing the threaded fastener 22 with the compression portion 48 having the compression portion diameter $D_{CP}$ being smaller than the threaded diameter or equal to threaded portion diameter $D_{TP}$, the compression portion 48 being either unthreaded between the head 44 and the threaded portion 50, threaded with threads continuing into the threaded portion 50, or unthreaded between the head 44 and the threaded portion 50 and the threaded fastener 22 including a second unthreaded portion 52 adjacent to the end 46.

The method of implantation further includes providing a compression transmission device 54 being cylindrical or non-cylindrical and including an exterior 56 having an exterior diameter $D_E$ and an interior 58 having an interior diameter $D_I$ defining an interior space for transmitting the compressional load of the threaded fastener 22 to the intramedullary nail 20, inserting the compression transmission device 54 into engagement with the near cortex hole 40 to prevent movement of the compression transmission device 54 relative to the near cortex hole 40, and extending the threaded fastener 22 through the compression transmission device 54 and the intramedullary nail 20 and through the far cortex hole 42 to extend transversely to the intramedullary nail 20 and threadedly engage the bore 34 to fixate the intramedullary nail 20 within the medullary canal 26.

Providing the compression transmission device 54 with the exterior diameter $D_E$ of a sufficient size to allow for mechanical strength without excessively weakening the bone 24 and an interior space being greater than the compression portion diameter $D_{CP}$ of the threaded fastener 22 provides space at least partially about the threaded fastener 22 and allows the fastener axis A to be variously disposed, i.e., eccentric, concentric, and/or skewed, relative to the interior space.

The method of the present invention is also used for implanting the intramedullary nail 20 into the medullary canal 26 surrounded by the cortex 28 when the cortex 28 of the bone 24 only includes the near cortex hole 40, as shown in FIG. 15. According to this embodiment, the method includes providing the bore 34 in the intramedullary nail 20, forming the near cortex hole 40 in the cortex 28, and providing the threaded fastener 22. The method further includes providing the compression transmission device 54, disposing the compression transmission device 54 in the near cortex hole 40, and contacting the intramedullary nail 20 with the compression transmission device 54. Once the compression transmission device 54 contacts the intramedullary nail 20, the method includes extending the threaded fastener 22 through the compression transmission device 54, and threadedly engaging the threaded portion 50 of the threaded fastener 22 to the intramedullary nail 20 along the bore 34. The interior space of the compression transmission device 54 is greater than the compression portion diameter $D_{CP}$ of the threaded fastener 22. The method also typically includes engaging the head 44 of the threaded fastener 22 and the compression transmission device 54.

The method can also include forming a far cortex hole 42 in the cortex 28, and extending the threaded portion 50 of the fastener 22 into the far cortex hole 42, as shown in FIGS. 5, 6, and 17-20. This embodiment also includes threadedly engaging the threaded portion 50 of the fastener 22 and the cortex 28 along the far cortex hole 42.

Another embodiment of the invention includes providing the counterbore surface 64 in the exterior surface of the intramedullary nail 20, as shown in FIGS. 16 and 17. In this embodiment, the step of contacting the intramedullary nail 20 with the compression transmission device 54 includes engaging the base surface 66. The method can alternatively include providing the countersink surface 68 in the exterior surface of the intramedullary nail 20, as shown in FIG. 18. In this embodiment, the step of contacting the intramedullary nail 20 with the compression transmission device 54 includes engaging the countersink surface 68.

The method of the present invention is also used to implant the intramedullary nail 20 into the medullary canal 26 surrounded by the cortex 28 when the cortex 28 of the bone 24 only includes the far cortex hole 42, as shown in FIG. 21. According to this embodiment, the method includes providing the bore 34 in the intramedullary nail 20, forming the far cortex hole 42 in the cortex 28, and providing the threaded fastener 22. The method also includes providing the compression transmission device 54, contacting the intramedullary nail 20 with the compression transmission device 54, extending the threaded fastener 22 through the compression transmission device 54 and the intramedullary nail 20, and threadedly engaging the threaded portion 50 of the threaded fastener 22 to the cortex 28 along the far cortex hole 42. In this embodiment, the interior space of the compression transmission device 54 is greater than the compression portion diameter $D_{CP}$ of the threaded fastener 22.

Figure 22:
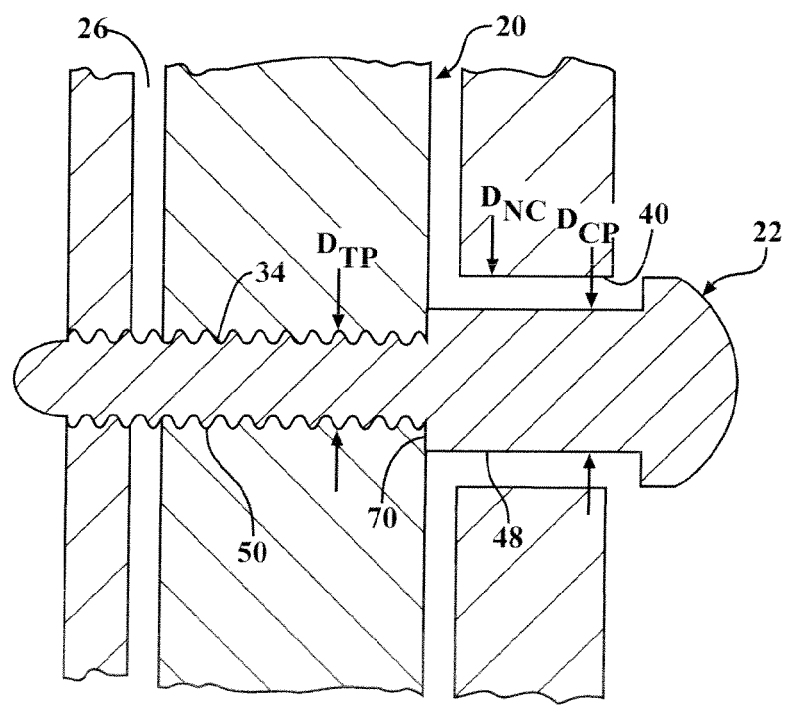
FIG. 22 is a cross-sectional view of a nail-fastener apparatus provided according to alternate embodiment of the invention.

Another aspect of the invention provides a method for implanting the intramedullary nail 20 into the medullary canal 26, wherein the compression portion diameter $D_{CP}$ of the compression portion 48 of the threaded fastener 22 is greater than the threaded portion diameter $D_{TP}$ of the threaded portion 50, as shown in FIG. 22. The greater diameter of the compression portion 48 provides a ledge 70 facing the threaded portion 48. The method includes forming the near cortex hole 40 with the near cortex hole diameter $D_{NC}$ being greater than the compression portion diameter $D_{CP}$ of the threaded fastener 22 so that the cortex 28 and the compression portion 48 provide a space therebetween. As shown in FIG. 22, the space is greater than the compression portion diameter $D_{CP}$. The method next includes inserting the threaded fastener 22 into the near cortex hole 40 and the bore 34 of the intramedullary nail 20, and threadedly engaging the threaded portion 50 of the threaded fastener 22 to the intramedullary nail 20 along the bore 34. The threaded fastener 22 is inserted into the bore 34 until the ledge 70 engages the exterior surface of the intramedullary nail 20 and the compression portion 48 of the threaded fastener 22 is disposed along the near cortex hole 40, as shown in FIG. 22. According to this method, no compression transmission device 54 is used. The stiffness of the nail-fastener apparatus can be adjusted by adjusting the size of the near cortex hole diameter $D_{NC}$ or the distance between the cortex 28 and the threaded portion 50 of the threaded fastener 22.

Obviously, many modifications and variations of the present invention are possible in light of the above teachings and may be practiced otherwise than as specifically described while within the scope of the appended claims. In addition, the reference numerals in the claims are merely for convenience and are not to be read in any way as limiting.

What is claimed is:

1. A nail-fastener apparatus for implantation into the medullary canal (26) surrounded by the cortex (28) of a bone (24) including a near cortex hole (40), comprising:
    an intramedullary nail (20) extending between a top end (30) and a bottom end (32) and defining a bore (34) for insertion into the medullary canal (26),
    a threaded fastener (22) including a head (44) and an end (46) with a threaded portion (50) extending along a fastener axis (A) therebetween for threadedly engaging said bore (34) of said intramedullary nail (20),
    said threaded fastener (22) including a compression portion (48) presenting a compression portion diameter ($D_{CP}$) and extending along said fastener axis (A) between said threaded portion (50) and said head (44) for extending through the near cortex hole (40) of the bone (24),
    a compression transmission device (54) extending longitudinally along said fastener axis (A) from a device top end (60) to a device bottom end (62),
    said compression transmission device (54) having an exterior (56) and an interior (58) defining an interior space, said interior (58) extending continuously from said device top end (60) to said device bottom end (62) and continuously around said fastener axis (A) and said compression portion (48) of said threaded fastener (22),
    said compression transmission device (54) being disposed between said head (44) of said threaded fastener (22) and said intramedullary nail (20), and
    said interior space being greater than said compression portion diameter ($D_{CP}$) of said fastener (22) for providing space at least partially about said threaded fastener (22) for allowing said fastener axis (A) to be variously disposed relative to said interior space.

2. A nail-fastener apparatus for implantation into the medullary canal (26) surrounded by the cortex (28) of a bone (24) including a near cortex hole (40), comprising:
    an intramedullary nail (20) extending between a top end (30) and a bottom end (32) and defining a bore (34) for insertion into the medullary canal (26),
    a threaded fastener (22) including a head (44) and an end (46) with a threaded portion (50) extending along a fastener axis (A) therebetween for threadedly engaging said bore (34) of said intramedullary nail (20),
    said threaded fastener (22) including a compression portion (48) presenting a compression portion diameter ($D_{CP}$) and extending along said fastener axis (A) between said threaded portion (50) and said head (44) for extending through the near cortex hole (40) of the bone (24),
    a compression transmission device (54) surrounding said compression portion (48) of said threaded fastener (22),
    said compression transmission device (54) having an exterior (56) and an interior (58) defining an interior space,
    said compression transmission device (54) being disposed between said head (44) of said threaded fastener (22) and said intramedullary nail (20),
    said interior space being greater than said compression portion diameter ($D_{CP}$) of said fastener (22) for providing space at least partially about said threaded fastener (22) for allowing said fastener axis (A) to be variously disposed relative to said interior space, and
    wherein the near cortex hole (40) has a near cortex hole diameter ($D_{NC}$), said exterior (56) of said compression transmission device (54) has an exterior diameter ($D_E$), and said exterior diameter ($D_E$) is equal to the near cortex hole diameter ($D_{NC}$) such that said exterior (56) of said compression transmission device (54) engages the cortex (28) along the near cortex hole (40).

3. A nail-fastener apparatus for implantation into the medullary canal (26) surrounded by the cortex (28) of a bone (24) including a near cortex hole (40), comprising:
    an intramedullary nail (20) extending between a top end (30) and a bottom end (32) and defining a bore (34) for insertion into the medullary canal (26),
    a threaded fastener (22) including a head (44) and an end (46) with a threaded portion (50) extending along a fastener axis (A) therebetween for threadedly engaging said bore (34) of said intramedullary nail (20),
    said threaded fastener (22) including a compression portion (48) presenting a compression portion diameter ($D_{CP}$) and extending along said fastener axis (A) between said threaded portion (50) and said head (44) for extending through the near cortex hole (40) of the bone (24),
    a compression transmission device (54) surrounding said compression portion (48) of said threaded fastener (22),
    said compression transmission device (54) having an exterior (56) and an interior (58) defining an interior space,
    said compression transmission device (54) being disposed between said head (44) of said threaded fastener (22) and said intramedullary nail (20),
    said interior space being greater than said compression portion diameter ($D_{CP}$) of said fastener (22) for providing space at least partially about said threaded fastener (22) for allowing said fastener axis (A) to be variously disposed relative to said interior space, and
    wherein the near cortex hole (40) has a near cortex hole diameter ($D_{NC}$), said exterior (56) of said compression transmission device (54) has an exterior diameter ($D_E$), and said exterior diameter ($D_E$) is less than the near cortex hole diameter ($D_{NC}$) such that said compression transmission device (54) and the cortex (28) provide a space therebetween.

4. A nail-fastener apparatus for implantation into the medullary canal (26) surrounded by the cortex (28) of a bone (24) including a near cortex hole (40), comprising:

an intramedullary nail (20) extending between a top end (30) and a bottom end (32) and defining a bore (34) for insertion into the medullary canal (26), a threaded fastener (22) including a head (44) and an end (46) with a threaded portion (50) extending along a fastener axis (A) therebetween for threadedly engaging said bore (34) of said intramedullary nail (20), said threaded fastener (22) including a compression portion (48) presenting a compression portion diameter ($D_{CP}$) and extending along said fastener axis (A) between said threaded portion (50) and said head (44) for extending through the near cortex hole (40) of the bone (24), a compression transmission device (54) surrounding said compression portion (48) of said threaded fastener (22), said compression transmission device (54) having an exterior (56) and an interior (58) defining an interior space, said compression transmission device (54) being disposed between said head (44) of said threaded fastener (22) and said intramedullary nail (20), said interior space being greater than said compression portion diameter ($D_{CP}$) of said fastener (22) for providing space at least partially about said threaded fastener (22) for allowing said fastener axis (A) to be variously disposed relative to said interior space, and wherein the cortex (28) includes a far cortex hole (42) having a far cortex hole diameter ($D_{FC}$), said threaded portion (50) of said threaded fastener (22) extends into the far cortex hole (42), said threaded portion (50) has a threaded portion diameter ($D_{TP}$), and said threaded portion diameter ($D_{TP}$) along the far cortex hole (42) is less than the far cortex hole diameter ($D_{FC}$) such that said threaded fastener (22) and the cortex (28) provide a space therebetween.

5. An apparatus as set forth in claim 4 wherein said threaded portion diameter ($D_{TP}$) of said threaded fastener (22) along said bore (34) of said intramedullary nail (20) is greater than said threaded portion diameter ($D_{TP}$) along the far cortex hole (42).

6. An apparatus as set forth in claim 1 wherein the cortex (28) includes a far cortex hole (42) and said threaded portion (50) of said threaded fastener (22) threadedly engages the cortex (28) along the far cortex hole (42).

7. A nail-fastener apparatus for implantation into the medullary canal (26) surrounded by the cortex (28) of a bone (24) including a near cortex hole (40), comprising:

an intramedullary nail (20) extending between a top end (30) and a bottom end (32) and defining a bore (34) for insertion into the medullary canal (26), a threaded fastener (22) including a head (44) and an end (46) with a threaded portion (50) extending along a fastener axis (A) therebetween for threadedly engaging said bore (34) of said intramedullary nail (20), said threaded fastener (22) including a compression portion (48) presenting a compression portion diameter ($D_{CP}$) and extending along said fastener axis (A) between said threaded portion (50) and said head (44) for extending through the near cortex hole (40) of the bone (24), a compression transmission device (54) surrounding said compression portion (48) of said threaded fastener (22), said compression transmission device (54) having an exterior (56) and an interior (58) defining an interior space, said compression transmission device (54) being disposed between said head (44) of said threaded fastener (22) and said intramedullary nail (20), said interior space being greater than said compression portion diameter ($D_{CP}$) of said fastener (22) for providing space at least partially about said threaded fastener (22) for allowing said fastener axis (A) to be variously disposed relative to said interior space, and wherein said compression transmission device (54) extends from a device top end (60) to a device bottom end (62), said device top end (60) engages said head (44) of said fastener (22), and said device bottom end (62) engages said intramedullary nail (20).

8. An apparatus as set forth in claim 7 wherein said intramedullary nail (20) has an exterior surface extending longitudinally along a center nail axis ($A_n$), said exterior surface presents a counterbore surface (64) extending perpendicular to said center nail axis ($A_n$) and to a base surface (66), said base surface (66) extends parallel to said center nail axis ($A_n$) and presents a base diameter ($D_b$) surrounding said bore (34), said bore (34) presents a bore diameter ($D_{BR}$), said base diameter ($D_b$) is greater than said bore diameter ($D_{BR}$), and said device bottom end (62) of said compression transmission device (54) engages said base surface (66).

9. An apparatus as set forth in claim 8 wherein said base surface (66) is convex and said device bottom end (62) of said compression transmission device (54) engages said base surface (66).

10. An apparatus as set forth in claim 8 wherein a washer (72) presenting a convex surface is disposed on said base surface (66) said device bottom end (62) of said compression transmission device (54) engages said convex surface of said washer (72).

11. An apparatus as set forth in claim 7 wherein said intramedullary nail (20) has an exterior surface extending longitudinally along a center nail axis ($A_n$), said exterior surface presents a countersink surface (68) extending at an angle relative to said center nail axis ($A_n$) and to said bore (34), said countersink surface (68) has a countersink diameter ($D_c$), said bore (34) presents a bore diameter ($D_{BR}$), said countersink diameter ($D_c$) is greater than said bore diameter ($D_{BR}$), and said device bottom end (62) of said compression transmission device (54) contacts said countersink surface (68).

12. A nail-fastener apparatus for implantation into the medullary canal (26) surrounded by the cortex (28) of a bone (24) including a near cortex hole (40), comprising:

an intramedullary nail (20) extending between a top end (30) and a bottom end (32) and defining a bore (34) for insertion into the medullary canal (26), a threaded fastener (22) including a head (44) and an end (46) with a threaded portion (50) extending along a fastener axis (A) therebetween for threadedly engaging said bore (34) of said intramedullary nail (20), said threaded fastener (22) including a compression portion (48) presenting a compression portion diameter ($D_{CP}$) and extending along said fastener axis (A) between said threaded portion (50) and said head (44) for extending through the near cortex hole (40) of the bone (24), a compression transmission device (54) surrounding said compression portion (48) of said threaded fastener (22), said compression transmission device (54) having an exterior (56) and an interior (58) defining an interior space, said compression transmission device (54) being disposed between said head (44) of said threaded fastener (22) and said intramedullary nail (20), said interior space being greater than said compression portion diameter ($D_{CP}$) of said fastener (22) for providing space at least partially about said threaded fastener

(22) for allowing said fastener axis (A) to be variously disposed relative to said interior space, and wherein said bore (34) of said intramedullary nail (20) is threaded and has a bore axis ($A_b$) extending between a near opening (36) and a far opening (38) transverse to said intramedullary nail (20) and presents a bore diameter ($D_{BR}$), said bore diameter ($D_{BR}$) includes a central bore diameter ($D_{CBR}$) disposed centrally between said near opening (36) and said far opening (38) of said bore (34), and said bore diameter ($D_{BR}$) increases from said central bore diameter ($D_{CBR}$) to said near opening (36) and from said central bore diameter ($D_{CBR}$) to said far opening (38) for allowing said fastener axis (A) to be skewed relative to said bore axis ($A_b$) while remaining threadedly engaged.

13. A nail-fastener apparatus for implantation into the medullary canal (26) surrounded by the cortex (28) of a bone (24) including a near cortex hole (40), comprising:

an intramedullary nail (20) extending between a top end (30) and a bottom end (32) and defining a bore (34) for insertion into the medullary canal (26), a threaded fastener (22) including a head (44) and an end (46) with a threaded portion (50) extending along a fastener axis (A) therebetween for threadedly engaging said bore (34) of said intramedullary nail (20), said threaded fastener (22) including a compression portion (48) presenting a compression portion diameter ($D_{CP}$) and extending along said fastener axis (A) between said threaded portion (50) and said head (44) for extending through the near cortex hole (40) of the bone (24), a compression transmission device (54) surrounding said compression portion (48) of said threaded fastener (22), said compression transmission device (54) having an exterior (56) and an interior (58) defining an interior space, said compression transmission device (54) being disposed between said head (44) of said threaded fastener (22) and said intramedullary nail (20), said interior space being greater than said compression portion diameter ($D_{CP}$) of said fastener (22) for providing space at least partially about said threaded fastener (22) for allowing said fastener axis (A) to be variously disposed relative to said interior space, and wherein said bore (34) of said intramedullary nail (20) is threaded and has a bore axis ($A_b$) extending between a near opening (36) and a far opening (38) transverse to said intramedullary nail (20) and presents a bore diameter ($D_{BR}$), and said bore diameter ($D_{BR}$) is consistent from said near opening (36) to said far opening (38).

14. A nail-fastener apparatus for implantation into the medullary canal (26) surrounded by the cortex (28) of a bone (24) including a far cortex hole (42), comprising:

an intramedullary nail (20) extending between a top end (30) and a bottom end (32) and defining a bore (34) for insertion into the medullary canal (26), a threaded fastener (22) including a head (44) and an end (46) with a threaded portion (50) extending along a fastener axis (A) therebetween for extending through said bore (34) of said intramedullary nail (20) and threadedly engaging the cortex (28) along the far cortex hole (42), said threaded fastener (22) including a compression portion (48) presenting a compression portion diameter ($D_{CP}$) and extending along said fastener axis (A) between said threaded portion (50) and said head (44), a compression transmission device (54) extending longitudinally along said fastener axis (A) from a from a device top end (60) to a device bottom end (62), said compression transmission device (54) having an exterior (56) and an interior (58) defining an interior space, said interior (58) extending continuously from said device top end (60) to said device bottom end (62) and continuously around said fastener axis (A) and said compression portion (48) of said threaded fastener (22), said compression transmission device (54) being disposed between said head (44) of said threaded fastener (22) and said intramedullary nail (20), and said interior space being greater than said compression portion diameter ($D_{CP}$) of said fastener (22) for providing space at least partially about said threaded fastener (22) for allowing said fastener axis (A) to be variously disposed relative to said interior space.

15. A nail-fastener apparatus for implantation into the medullary canal (26) surrounded by the cortex (28) of a bone (24) including a near cortex hole (40), comprising:

an intramedullary nail (20) extending between a top end (30) and a bottom end (32) and defining a bore (34) for insertion into the medullary canal (26), a fastener (23) including a head (44) and an end (46) with a first portion (51) extending along a fastener axis (A) therebetween for frictionally engaging said bore (34) of said intramedullary nail (20), said fastener (23) including a compression portion (48) presenting a compression portion diameter ($D_{CP}$) and extending along said fastener axis (A) between said first portion (51) and said head (44) for extending through the near cortex hole (40) of the bone (24), a compression transmission device (54) extending longitudinally along said fastener axis (A) from a from a device top end (60) to a device bottom end (62), said compression transmission device (54) having an exterior (56) and an interior (58) defining an interior space, said interior (58) extending continuously from said device top end (60) to said device bottom end (62) and continuously around said fastener axis (A) and said compression portion (48) of said fastener (23), said compression transmission device (54) being disposed between said head (44) of said fastener (23) and said intramedullary nail (20), and said interior space being greater than said compression portion diameter ($D_{CP}$) of said fastener (23) for providing space at least partially about said fastener (23) for allowing said fastener axis (A) to be variously disposed relative to said interior space.

16. A nail-fastener apparatus for implantation into the medullary canal (26) surrounded by the cortex (28) of a bone (24) including a far cortex hole (42), comprising:

an intramedullary nail (20) extending between a top end (30) and a bottom end (32) and defining a bore (34) for insertion into the medullary canal (26), a fastener (23) including a head (44) and an end (46) with a first portion (51) extending along a fastener axis (A) therebetween for extending through said bore (34) of said intramedullary nail (20) and frictionally engaging the cortex (28) along the far cortex hole (42), said fastener (23) including a compression portion (48) presenting a compression portion diameter ($D_{CP}$) and extending along said fastener axis (A) between said first portion (51) and said head (44), a compression transmission device (54) extending longitudinally along said fastener axis (A) from a from a device top end (60) to a device bottom end (62), said compression transmission device (54) having an exterior (56) and an interior (58) defining an interior space, said interior (58) extending continuously from said device top end (60) to said device bottom end (62) and continuously around said fastener axis (A) and said compression portion (48) of said fastener (23), said compression transmission device (54) being disposed between said head (44) of said fastener (23) and said intramedullary nail (20), and said interior space being greater than said compression portion diameter ($D_{CP}$) of said fastener (23) for providing space at least partially about said fastener (23) for allowing said fastener axis (A) to be variously disposed relative to said interior space.

17. A method for implanting an intramedullary nail (20) into the medullary canal (26) surrounded by the cortex (28) of the bone (24) comprising the steps of:

providing a bore (34) in the intramedullary nail (20) including threads, forming a near cortex hole (40) in the cortex (28), providing a threaded fastener (22) including a head (44) and an end (46) with a compression portion (48) presenting a compression portion diameter ($D_{CP}$) and a threaded portion (50) extending along a fastener axis (A) between the head (44) and the end (46), providing a compression transmission device (54) having an exterior (56) and an interior (58) defining an interior space, disposing the compression transmission device (54) in the near cortex hole (40) and contacting the intramedullary nail (20) with the compression transmission device (54), extending the threaded fastener (22) through the compression transmission device (54), threadedly engaging the threaded portion (50) of the threaded fastener (22) to the intramedullary nail (20) along the bore (34), and providing the compression transmission device (54) with the interior space being greater than the compression portion diameter ($D_{CP}$) of the threaded fastener (22) for providing space at least partially about the threaded fastener (22) for allowing the fastener axis (A) to be variously disposed relative the interior space.

18. A method as set forth in claim 17 including engaging the head (44) of the threaded fastener (22) and the compression transmission device (54).

19. A method as set forth in claim 17 wherein the near cortex hole (40) has a near cortex hole diameter ($D_{NC}$), the exterior (56) of the compression transmission device (54) presents an exterior diameter ($D_E$), and including the step of providing the exterior diameter ($D_E$) equal to the near cortex hole diameter ($D_{NC}$) such that the exterior (56) of the compression transmission device (54) engages the cortex (28) along the near cortex hole (40).

20. A method as set forth in claim 17 wherein the near cortex hole (40) presents a near cortex hole diameter ($D_{NC}$), the exterior (56) of the compression transmission device (54) presents an exterior diameter ($D_E$), and including the step of providing the exterior diameter ($D_E$) to be less than the near cortex hole diameter ($D_{NC}$) such that the exterior (56) of the compression transmission device (54) and the cortex (28) define a space therebetween.

21. A method as set forth in claim 17 wherein the threaded portion (50) presents a threaded portion diameter ($D_{TP}$), and including the steps of forming a far cortex hole (42) in the cortex (28) presenting a far cortex hole diameter ($D_{FC}$) being greater than the threaded portion diameter ($D_{TP}$), extending the threaded portion (50) of the fastener (22) into the far cortex hole (42) such that the threaded fastener (22) and the cortex (28) define a space therebetween along the far cortex hole (42).

22. A method as set forth in claim 21 including the step of providing the threaded portion diameter ($D_{TP}$) of the threaded fastener (22) along the bore (34) of the intramedullary nail (20) to be greater than the threaded portion diameter ($D_{TP}$) along the far cortex hole (42).

23. A method as set forth in claim 17 including the steps of forming a far cortex hole (42) in the cortex (28) and threadedly engaging the threaded portion (50) of the threaded fastener (22) and the cortex (28) along the far cortex hole (42).

24. A method as set forth in claim 17 wherein the intramedullary nail (20) has an exterior surface extending longitudinally along a center nail axis ($A_n$), the bore (34) has a bore diameter ($D_{BR}$), and including the steps of providing a counterbore surface (64) in the exterior surface of the intramedullary nail (20), the step of providing the counterbore surface (64) includes providing the counterbore surface (64) perpendicular to the center nail axis ($A_n$) to a base surface (66), providing the base surface (66) to extend parallel to the center nail axis ($A_n$) and present a base diameter ($D_b$) surrounding the bore (34), providing the base diameter ($D_b$) to be greater than the bore diameter ($D_{BR}$), and wherein the step of contacting the intramedullary nail (20) with the compression transmission device (54) includes engaging the base surface (66).

25. A method as set forth in claim 17 wherein the intramedullary nail (20) has an exterior surface extending longitudinally along a center nail axis ($A_n$), the bore (34) has a bore diameter ($D_{BR}$), and including the steps of providing a countersink surface (68) having a countersink diameter ($D_c$) in the exterior surface, the step of providing the countersink surface (68) includes providing the countersink surface (68) at an angle relative to the center nail axis ($A_n$) to the bore (34), providing the countersink diameter ($D_c$) to be greater than the bore diameter ($D_{BR}$), and wherein the step of contacting the intramedullary nail (20) with the compression transmission device (54) includes engaging the countersink surface (68).

26. A method as set forth in claim 17 wherein the bore (34) includes a near opening (36) and a far opening (38), and including the steps of providing the bore (34) to include a bore diameter ($D_{BR}$) at the near opening (36) and the far opening (38) and a central bore diameter ($D_{CBR}$) between the openings (36, 38), and wherein the bore diameter ($D_{BR}$) increases from the central bore diameter ($D_{CBR}$) to the near opening (36) and from the central bore diameter ($D_{CBR}$) to the far opening (38) for allowing the fastener axis (A) to be skewed relative to the bore axis ($A_b$) while remaining threadedly engaged.

27. A method as set forth in claim 17 wherein the bore (34) of the intramedullary nail (20) is threaded and has a bore axis ($A_b$) extending between a near opening (36) and a far opening (38) transverse to the intramedullary nail (20) and presents a bore diameter ($D_{BR}$), and the bore diameter ($D_{BR}$) is consistent from said near opening (36) to the far opening (38).

28. A method for implanting an intramedullary nail (20) into the medullary canal (26) surrounded by the cortex (28) of the bone (24) comprising the steps of:

providing a bore (34) in the intramedullary nail (20) including threads, forming a far cortex hole (42) in the cortex (28), providing a threaded fastener (22) including a head (44) and an end (46) with a compression portion (48) having a compression portion diameter ($D_{CP}$) and a threaded portion (50) extending along a fastener axis (A) therebetween, providing a compression transmission device (54) having an exterior (56) and an interior (58) defining an interior space, contacting the intramedullary nail (20) with the compression transmission device (54), extending the threaded fastener (22) through the compression transmission device (54) and the bore (34) of the intramedullary nail (20), threadedly engaging the threaded portion (50) of the threaded fastener (22) to the cortex (28) along the far cortex hole (42), and providing the compression transmission device (54) with the interior space being greater than the compression portion diameter ($D_{CP}$) of the threaded fastener (22) for providing space at least partially about the threaded fastener (22) for allowing the fastener axis (A) to be variously disposed relative the interior space.

29. A method for implanting an intramedullary nail (20) into the medullary canal (26) surrounded by the cortex (28) of the bone (24) comprising the steps of:

providing a bore (34) in the intramedullary nail (20) including threads, providing a threaded fastener (22) including a head (44) and an end (46) with a compression portion (48) presenting a compression portion diameter ($D_{CP}$) and a threaded portion (50) presenting a threaded portion diameter ($D_{TP}$) extending along a fastener axis (A), wherein the threaded portion (50) is disposed between the compression portion (48) and the end (46) and the compression portion diameter ($D_{CP}$) is greater than the threaded portion diameter ($D_{TP}$), forming a near cortex hole (40) in the cortex (28) having a near cortex hole diameter ($D_{NC}$) being greater than the compression portion diameter ($D_{CP}$), extending the threaded fastener (22) through the near cortex hole (40) and into the bore (34) until the compression portion (48) engages the intramedullary nail (20), and threadedly engaging the threaded portion (50) of the threaded fastener (22) to the intramedullary nail (20) along the bore (34).

30. A method for implanting an intramedullary nail (20) into the medullary canal (26) surrounded by the cortex (28) of the bone (24) comprising the steps of:

providing a bore (34) in the intramedullary nail (20), forming a near cortex hole (40) in the cortex (28), providing a fastener (23) including a head (44) and an end (46) with a compression portion (48) presenting a compression portion diameter ($D_{CP}$) and a first portion (51) extending along a fastener axis (A) between the head (44) and the end (46), providing a compression transmission device (54) having an exterior (56) and an interior (58) defining an interior space, disposing the compression transmission device (54) in the near cortex hole (40) and contacting the intramedullary nail (20) with the compression transmission device (54), extending the fastener (23) through the compression transmission device (54), frictionally engaging the first portion (51) of the fastener (23) to the intramedullary nail (20) along the bore (34), and providing the compression transmission device (54) with the interior space being greater than the compression portion diameter ($D_{CP}$) of the fastener (23) for providing space at least partially about the fastener (23) for allowing the fastener axis (A) to be variously disposed relative the interior space.

31. A method for implanting an intramedullary nail (20) into the medullary canal (26) surrounded by the cortex (28) of the bone (24) comprising the steps of:

providing a bore (34) in the intramedullary nail (20), forming a far cortex hole (42) in the cortex (28), providing a fastener (23) including a head (44) and an end (46) with a compression portion (48) having a compression portion diameter ($D_{CP}$) and a first portion (51) extending along a fastener axis (A) therebetween, providing a compression transmission device (54) having an exterior (56) and an interior (58) defining an interior space, contacting the intramedullary nail (20) with the compression transmission device (54), extending the fastener (23) through the compression transmission device (54) and the bore (34) of the intramedullary nail (20), frictionally engaging the first portion (51) of the fastener (23) to the cortex (28) along the far cortex hole (42), and providing the compression transmission device (54) with the interior space being greater than the compression portion diameter ($D_{CP}$) of the fastener (23) for providing space at least partially about the fastener (23) for allowing the fastener axis (A) to be variously disposed relative the interior space.

\* \* \* \* \*